(12) United States Patent
McAlpine et al.

(10) Patent No.: US 10,405,963 B2
(45) Date of Patent: Sep. 10, 2019

(54) METHOD OF PRODUCING A 3D SUBJECT SPECIFIC BIOMIMETIC NERVE CONDUIT

(71) Applicant: TRUSTEES OF PRINCETON UNIVERSITY, Princeton, NJ (US)

(72) Inventors: Michael C. McAlpine, Minneapolis, MN (US); Blake N. Johnson, Plainsboro, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 540 days.

(21) Appl. No.: 14/942,714

(22) Filed: Nov. 16, 2015

(65) Prior Publication Data
US 2017/0135802 A1 May 18, 2017

(51) Int. Cl.
| | |
|---|---|
| B29C 41/02 | (2006.01) |
| A61F 2/04 | (2013.01) |
| A61L 27/24 | (2006.01) |
| A61L 27/22 | (2006.01) |
| A61L 27/20 | (2006.01) |
| A61L 27/18 | (2006.01) |
| A61L 27/52 | (2006.01) |
| A61L 27/54 | (2006.01) |
| A61L 27/36 | (2006.01) |
| B29C 64/112 | (2017.01) |
| A61L 27/38 | (2006.01) |
| A61B 17/11 | (2006.01) |
| A61B 34/10 | (2016.01) |
| A61B 17/00 | (2006.01) |
| A61B 90/00 | (2016.01) |

(52) U.S. Cl.
CPC ............ *A61F 2/04* (2013.01); *A61B 17/1128* (2013.01); *A61B 34/10* (2016.02); *A61L 27/18* (2013.01); *A61L 27/20* (2013.01); *A61L 27/222* (2013.01); *A61L 27/24* (2013.01); *A61L 27/3675* (2013.01); *A61L 27/383* (2013.01); *A61L 27/3878* (2013.01); *A61L 27/52* (2013.01); *A61L 27/54* (2013.01); *B29C 64/112* (2017.08); *A61B 2017/00526* (2013.01); *A61B 2017/1132* (2013.01); *A61B 2034/105* (2016.02); *A61B 2034/108* (2016.02); *A61B 2090/373* (2016.02); *A61F 2230/0069* (2013.01); *A61F 2240/002* (2013.01); *A61F 2250/0067* (2013.01); *A61L 2300/414* (2013.01); *A61L 2300/432* (2013.01); *A61L 2430/32* (2013.01)

(58) Field of Classification Search
CPC .... B29C 64/106; B29C 64/112; B29C 64/118
USPC ................................................ 264/129, 308
See application file for complete search history.

(56) References Cited

U.S. PATENT DOCUMENTS

| | | | | |
|---|---|---|---|---|
| 2002/0086047 | A1* | 7/2002 | Mueller | A61B 17/1128 424/426 |
| 2006/0257377 | A1* | 11/2006 | Atala | A61K 38/18 424/93.7 |
| 2008/0125870 | A1 | 5/2008 | Carmichael et al. | |
| 2008/0208358 | A1* | 8/2008 | Bellamkonda | A61L 27/16 623/23.72 |
| 2014/0257518 | A1 | 9/2014 | McAlpine et al. | |
| 2015/0224226 | A1* | 8/2015 | Bhatia | C12N 5/0068 435/1.1 |

OTHER PUBLICATIONS

Kong, Yong Lin et al., "3D Printed Quantum Dot Light-Emitting Diodes," Nano Letters, vol. 14, 2014, pp. 7017-7023.
Pateman, Christopher J. et al., "Nerve Guides Manufactured from Photocurable Polymers to Aid Peripheral Nerve Repair," Biomaterials, vol. 49, 2015, pp. 77-89.
Johnson, Blake N. et al., "3D Printed Anatomical Nerve Regeneration Pathways," Advanced Functional Materials, 2015, pp. 1-13.
Johnson, Blake N. et al., "Supporting Information 3D Printed Anatomical Nerve Regeneration Pathways," Advanced Functional Materials, 2015, pp. 1-11.

* cited by examiner

*Primary Examiner* — Leo B Tentoni
(74) *Attorney, Agent, or Firm* — Fisherbroyles, LLP

(57) ABSTRACT

The present invention includes biomimetic nerve conduits that can be used as nerve regeneration pathways. The present invention further provides methods of preparing and using biomimetic nerve conduits. The disclosed compositions and methods have a broad range of potential applications, for example replacing a missing or damaged section of a nerve pathway of a mammal.

25 Claims, 16 Drawing Sheets

I) Tissue Model

II) 3D Scanning

III) 3D Printing

METHOD OF PRODUCING A 3D SUBJECT SPECIFIC BIOMIMETIC NERVE CONDUIT

STATEMENT REGARDING FEDERALLY SPONSORED RESEARCH OR DEVELOPMENT

This invention was made with government support under Grant No. D12AP00245 awarded by the Department of the Interior. The government has certain rights in the present invention.

BACKGROUND

Efforts to personalize regenerative approaches, therapeutics, and biomedical devices are catalyzing major advances in the treatment of serious injuries and chronic diseases. State of the art efforts in personalized medicine, which are common within certain areas in the biomedical space (e.g., dentistry), now extend toward development of patient-specific tissues and organs, drug screening approaches, and advanced biomedical devices (e.g., advanced prosthetics and biointerfaces). Customization of medical treatments could convey significant advantages by targeting treatment directly to a specific injury or disease profile of a patient, which is critical due to inherent variance in patient anatomies, injury profiles, and genetic and proteomic structures. Recent advances in genome and proteome mapping are enabling advances in personalized treatment approaches at the molecular level. Yet, it remains a critical challenge to provide customized treatments at the tissue level that address patient-to-patient variances in disease and injury profiles, particularly in neuroregeneration.

Nerve regeneration is a complex biological phenomena that often requires a balance of molecular- and tissue-level repair strategies, depending on the nature of the particular injury or neurological disorder. Peripheral nerve regeneration is a particularly important concern, as damage to peripheral nerves occurs via various mechanisms, including disease and traumatic accidents such as car accidents and battlefield wounds, resulting in greater than 200,000 annual nerve repair procedures performed in the U.S. alone. Conventional nerve repair techniques center on grafting approaches, such as autografts and decellularized allografts, which have the major advantages of closely mimicking natural nerve characteristics. However, grafting approaches also present various drawbacks and limitations, including the need for an additional harvesting surgery, chronic pain and morbidity at the donor site, limitations on graft size and geometry, and potential immune response. This has motivated alternative nerve repair strategies, such as the use of nerve guidance channels constructed from synthetic and biological polymers, which provide a geometric tubular pathway for the reconnection and regeneration of damaged nerves.

Nerve guidance channels possess various advantages, including flexibility in material choice, avoidance of additional surgeries, and the ability to augment guide characteristics with physical, cellular, and biochemical functionalities. Existing nerve guide technologies have facilitated the regeneration of short linear nerve injuries, but the technology is hindered in its application to more complex injuries. This is because the nerve guidance channel manufacturing approaches, such as molding, solid-liquid phase-separation, electrospinning, and lyophilizing, rely on structure-providing scaffolds that are later removed. This significantly hinders the ability to achieve complex 3D geometries and incorporate supporting biomodalities. Thus, the development of a one-pot biomanufacturing approach to nerve guide design and fabrication, which enables programmable, complex geometries and biomimetic augmentation, may significantly expand the scope of nerve channel-based regeneration strategies.

There is a need in the art for novel compositions and methods for promoting nerve regeneration in a mammal in need thereof. In certain embodiments, such compositions and methods should allow for the regeneration of multiple and complex nerve pathways. The present invention meets this need.

BRIEF SUMMARY

The present invention provides a biomimetic nerve conduit. The present invention further provides a method of promoting nerve regeneration in a mammal in need thereof, wherein a section of one of the mammal's nerve pathway is missing or damaged thus generating at least two severed nerve pathway extremities. The present invention further provides a system for producing a 3D subject-specific biomimetic nerve conduit, which is used to replace a missing or damaged section of a nerve pathway of a mammal. The present invention further provides a method of producing a 3D subject-specific biomimetic nerve conduit, which is used to replace a missing or damaged section of a nerve pathway of a mammal.

In certain embodiments, the conduit of the invention comprises a central tube, wherein the central tube comprises a primary tube wall that defines a primary lumen therein, and wherein both ends of the central tube are open. In other embodiments, the conduit of the invention further comprises at least one branching tube, wherein the at least one branching tube comprises a secondary tube wall that defines a secondary lumen therein. In yet other embodiments, the proximal end of the at least one branching tube is physically attached to the primary tube wall of the central tube. In yet other embodiments, the secondary lumen of the at least one branching tube is in fluid communication with the primary lumen of the central tube. In yet other embodiments, the distal end of the at least one branching tube is open.

In certain embodiments, the central tube and/or the at least one branching tube has/have a length ranging from about 0.1 cm to about 100 cm.

In certain embodiments, the primary tube wall of the central tube and the secondary tube wall of the at least one branching tube independently comprise at least one material selected from the group consisting of a synthetic polymer and a biopolymer. In other embodiments, the primary tube wall of the central tube and the secondary tube wall of the at least one branching tube both comprise a material selected from the group consisting of a synthetic polymer and a biopolymer. In yet other embodiments, the primary tube wall of the central tube and the secondary tube wall of the at least one branching tube are made of a same material.

In certain embodiments, the inner surface of the primary tube wall of the central tube comprises a plurality of longitudinally extending indentations. In other embodiments, the inner surface of the secondary tube wall of the at least one branching tube comprises a plurality of longitudinally extending indentations. In yet other embodiments, the inner surface of the primary tube wall of the central tube comprises a plurality of longitudinally extending indentations, and wherein the inner surface of the secondary tube wall of the at least one branching tube comprises a plurality of longitudinally extending indentations.

In certain embodiments, the biomimetic nerve conduit has approximately the same Young's modulus as a mammal's nerve pathway.

In certain embodiments, the lumen of at least one selected from the group consisting of the central tube and the at least one branched tube independently contains a hydrogel. In other embodiments, the hydrogel is independently selected from the group consisting of gelatin, methacrylated gelatin, polyethylene glycol, collagen, alginate, hyaluronic acid and any combinations thereof. In yet other embodiments, the hydrogel comprises an agent selected from a micro RNA, a single stranded DNA, a double stranded DNA, a cell, a filler, a therapeutic drug, a chemoattractant, a biocide, a peptide, a protein, a chemoattractant, a catalyst, and any combinations thereof. In yet other embodiments, the hydrogel comprises at least one selected from the group consisting of nerve growth factor (NGF), glial cell line-derived neurotrophic factor (GDNF) and vascular endothelial growth factor (VEGF).

In certain embodiments, the primary lumen of the central tube and the secondary lumen of the at least one branched tube independently contain a hydrogel. In other embodiments, the hydrogel in the primary lumen of the central tube is different from the hydrogel in the secondary lumen of the at least one branched tube. In yet other embodiments, the hydrogel is independently present as a plurality of droplets that are distributed in a spatial relationship along the longitudinal dimension of the tube. In yet other embodiments, each one of the plurality of droplets occupies the whole cross section of the lumen where it is located. In yet other embodiments, the plurality of hydrogel droplets are uniformly spaced along the longitudinal direction of the tube. In yet other embodiments, the plurality of hydrogel droplets are not uniformly spaced along the longitudinal direction of the tube. In yet other embodiments, the spacing between consecutive hydrogel droplets along the longitudinal dimension of the at least one branching tube is greater near the proximal end than near the distal end of the tube. In yet other embodiments, the spacing between consecutive hydrogel droplets along the longitudinal dimension of the at least one branching tube is greater near the distal end than near the proximal end of the tube.

In certain embodiments, the method comprises physically connecting the at least two severed nerve pathway extremities using at least one biomimetic nerve conduit of the present invention. In other embodiments, the biomimetic nerve conduit has a geometry corresponding to the missing or damaged section of the mammal's nerve pathway. In yet other embodiments, the biomimetic nerve conduit is 3D printed based on a 3D computer model of the missing or damaged section of the mammal's nerve pathway. In yet other embodiments, the 3D computer model is generated by scanning the area where the missing or damaged section of the mammal's nerve pathway is located in the mammal. In yet other embodiments, the 3D computer model is generated by analyzing the nerve pathways of a similar mammal. In yet other embodiments, the biomimetic nerve conduit is generated using a layer-by-layer fused deposition 3D printing method.

In certain embodiments, a plurality of longitudinally extending indentations are present along the inner surface of at least one tube wall of the biomimetic nerve conduit. In other embodiments, the plurality of longitudinally extending indentations have at least one geometry selected from the group consisting of a microgroove and a fiber. In yet other embodiments, at least one of the plurality of longitudinally extending indentations has a geometry corresponding to a band of Büngner. In yet other embodiments, at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell. In yet other embodiments, a plurality of droplets are distributed in a spatial relationship along the longitudinal dimension of at least one tube. In yet other embodiments, the plurality of hydrogel droplets contain an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets. In yet other embodiments, the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit. In yet other embodiments, the biomimetic nerve conduit comprises a motor branch and a sensory branch.

In certain embodiments, the system comprises an imaging system configured to generate a 3D image of the missing or damaged section of the nerve pathway of the mammal or a 3D image of the intact nerve pathway of a similar mammal. In other embodiments, the system comprises a modeling system configured to generate a corresponding 3D computer model from the 3D image of the missing or damaged section of the nerve pathway of the mammal or a 3D image of the intact nerve pathway of a similar mammal. In yet other embodiments, the system comprises a 3D printer configured to generate at least one biomimetic nerve conduit of the invention. In yet other embodiments, the biomimetic nerve conduit has a geometry corresponding to the missing or damaged section of the nerve pathway of the mammal, and wherein the biomimetic nerve conduit comprises at least one motor branch and at least one sensory branch. In yet other embodiments, the 3D printer allows for a plurality of longitudinally extending indentations to be present along the inner surface of at least one tube wall of the biomimetic nerve conduit. In yet other embodiments, the plurality of longitudinally extending indentations have at least one geometry selected from the group consisting of a microgroove and a fiber. In yet other embodiments, at least one of the plurality of longitudinally extending indentations has a geometry corresponding to a band of Büngner. In yet other embodiments, at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell. In yet other embodiments, the 3D printer allows for a plurality of droplets to be distributed in a spatial relationship along the longitudinal dimension of at least one tube. In yet other embodiments, the plurality of hydrogel droplets contain an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets. In yet other embodiments, the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit.

In certain embodiments, the method comprises obtaining a primary 3D image selected from the group consisting of: the missing or damaged section of the nerve pathway of the mammal; and the intact nerve pathway of a similar mammal. In other embodiments, the method comprises generating a 3D computer model from the primary 3D image. In yet other embodiments, the method comprises using the 3D computer model to 3D print a biomimetic nerve conduit that has a geometry corresponding to the missing or damaged section of the mammal's nerve pathway, wherein the biomimetic nerve conduit comprises at least one motor branch and at least one sensory branch. In yet other embodiments, a plurality of longitudinally extending indentations is present along the inner surface of at least one tube wall of the biomimetic nerve conduit. In yet other embodiments, the plurality of longitudinally extending indentations have at least one geometry selected from the group consisting of a microgroove and a fiber. In yet other embodiments, at least one of the plurality of longitudinally extending indentations has a geometry corresponding to a band of Büngner. In yet other embodiments, at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell. In yet other embodiments, a plurality of droplets is distributed in a spatial relationship along the longitudinal dimension of at least one tube. In yet other embodiments, the plurality of hydrogel droplets contain an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets. In yet other embodiments, the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit.

BRIEF DESCRIPTION OF THE FIGURES

For the purpose of illustrating the present invention, there are depicted in the drawings certain embodiments in accordance with the present invention. However, the present invention is not limited to the precise arrangements and instrumentalities of the embodiments depicted in the drawings.

FIG. 1A: A tissue model of the nerve pathway to be constructed is prepared for subsequent imaging by either incision (in situ approach) or transection (ex situ approach). FIG. 1B: The intact or transected tissue is imaged using structured light scanning (SLS), which results in a high precision 3D model of the nerve pathway. FIG. 1C: The reverse engineered nerve pathway is 3D printed, which provides a realized device that mimics the original nerve in terms of geometry, physical cues, and path-specific biochemical cues in the form of gradient distributions.

FIG. 2A: The sciatic nerve serves as a model for the custom nerve pathway, as it provides a bifurcating mixed nerve model that branches into distinct sensory (sural nerve; top) and motor (peroneal and tibial; middle and bottom, respectively) paths. FIG. 2B: The complex nerve pathway is transected, providing a tissue template for ex situ scanning measurements. FIG. 2C: Scans are conducted from various perspectives in order to assemble a full 3D model that comprehensively describes the geometry of the nerve pathway (sural and tibial branches). FIG. 2D: The individual scans are aligned to replicate the 3D geometry of the nerve tissue. FIG. 2E: The aligned scans are assembled into a watertight 3D model leading to a full reconstruction of the nerve pathway geometry, which provides a template for both finite element analysis (FEA) and 3D printing. FIG. 2F: The 3D model is printed into a hollow silicone pathway that is customized to fit the exact geometry of the original tissue.

FIG. 3A: Tensile strength measurements on 3D printed materials reveal the influence of the printing orientation (physical cue direction) on the ultimate tensile strength. FIG. 3B: Von Mises stress ($\sigma$) distribution in the nerve pathway under a tensile load applied to the distal ends of the nerve ($\sigma_{max}$=0.41 MPa). FIG. 3C: Von Mises stress ($\sigma$) distribution in the nerve pathway under a torsional load applied to the distal ends of the nerve ($\sigma_{max}$=0.61 MPa).

FIG. 4A: Scanning electron micrograph of a representative 3D printed hollow nerve pathway displaying an axially-oriented physical cue on the luminal surface. FIG. 4B: Profilometry measurement performed on the luminal surface of the 3D printed nerve pathway shows a distinct microgroove structure. FIG. 4C: Cultured primary embryonic neurons on the 3D printed horizontally-oriented physical cue (90° reference angle) stained for Tau (green). FIG. 4D: Corresponding orientation analysis showing a coincidence of the neurite network alignment with the physical cue. FIG. 4E: Cultured Schwann cells on the horizontally-oriented physical cue (90° reference angle) stained for GFAP (green) and laminin (red). FIG. 4F: Corresponding orientation analysis showing a coincidence of the cytoskeleton and extracellular matrix alignment with the physical cue.

FIG. 5A: Schematic of the path-specific incorporation of gradient distributions of selective biochemical cues—nerve growth factor, NGF, and glial cell line-derived neurotrophic factor, GDNF—in the sensory and motor paths, respectively. FIG. 5B: Representative photograph of the 3D printed gradient pattern achieved using a protein-loaded hydrogel. A green dye was added to the hydrogel to enhance the image contrast. FIG. 5C: Results from finite element analysis (FEA) of transient drug release showing the establishment of an axially-oriented concentration gradient that results from the 3D printed luminal hydrogel pattern over time. FIG. 5D: Experimental drug release studies showing the protein release kinetics from the gelatin hydrogel system.

FIG. 6A: Effect of the diffusive NGF gradient on the guidance of the sensory neurite network growth (inset scale bar=1,000 μm). FIG. 6B: Effect of the diffusive GDNF gradient on the migration velocity of Schwann cells (inset scale bar=100 μm; arrow indicates direction of source and migration direction). FIG. 6C: Functional return in rat hind limbs: comparison of gait duty cycle in the regenerated limb. In all images, single asterisk indicates p-value <0.05; double asterisk indicates p-value <0.01.

FIG. 7A: Photograph of the scanned sciatic nerve bifurcation (yellow box indicates the scanned region). FIG. 7B: Scan data obtained from in situ imaging.

FIG. 8A: Tear-based failure mechanism observed when the tensile load was applied against the 3D printed grain. FIG. 8B: Rip-based failure mechanism observed when the tensile load was applied with the 3D printed grain.

DETAILED DESCRIPTION OF THE PRESENT INVENTION

Figure 1A:
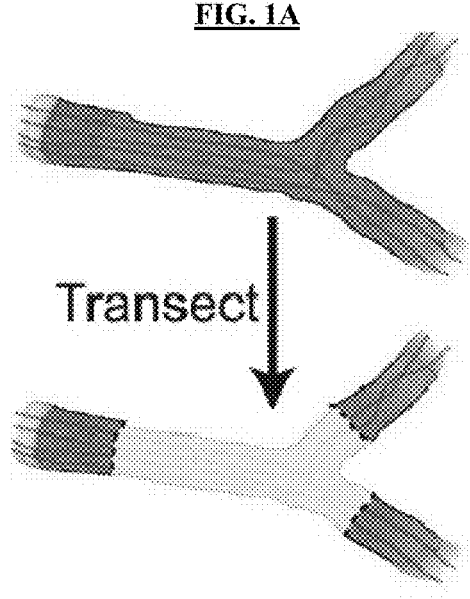
FIGS. 1A-1C illustrate non-limiting personalized nerve regeneration pathways enabled by 3D scanning and printing.

The present invention provides in certain aspects a novel 3D printing approach for nerve regeneration pathways that are personalized to anatomical geometry. The compositions and methods of the present invention allow for the use of physical and biochemical cues to promote the simultaneous regeneration of multiple nerve pathways. In certain embodiments, the biomimetic nerve conduits of the present invention match the final pathway geometric design to the original tissue structure. In other embodiments, the biomimetic nerve conduits of the present invention incorporate physical and biochemical cues in the form of, respectively, microgrooves and multicomponent diffusive biomolecular gradients. The biomimetic nerve conduits of the present invention can be used to treat and/or heal complex mixed nerve injuries.

3D printing is a computer-driven, robotics-based biomanufacturing approach that is a valuable tool in the development of customized biomedical devices. 3D printing has catalyzed novel efforts in the manufacturing of artificial tissues and organs, electronics, and biomedical devices. 3D printing is also by nature a serial process, which may be used towards customized manufacturing and biomedical applications. Furthermore, the coupling of 3D printing approaches with 3D imaging technologies, along with its compatibility with a multivariate material set, including metals, synthetic polymers, biomaterials, and nanomaterials, makes it a particularly exciting and expansive tool in next-generation biomanufacturing initiatives.

As described herein, a 3D printing approach to the design and manufacturing of nerve guidance pathways provides new opportunities for advanced nerve repair via the production of anatomically accurate and complex geometries, as well as programmable incorporation of biomimetic physical and biochemical functionalities. The present disclosure demonstrates the combination of 3D imaging and 3D printing for the design, optimization, and biomanufacturing of anatomically-true biomimetic custom nerve regeneration pathways. Specifically, the creation of custom pathways generated from nonlinear anatomical geometries, and the incorporation of physical cues in the form of microgrooves, and path-specific multicomponent biochemical cues in the form of spatiotemporal growth factor gradients were demonstrated. The application of this complex nerve guide technology to regenerating bifurcating mixed nerve pathways was examined using the original tissue structure as a template for the pathway geometry. Specific features offered by the new manufacturing approach include biomimicry of natural anatomical structure, introduction of guiding physical cues, and the implementation of path-specific biomimetic multicomponent gradients within the scaffold architecture. In certain embodiments, this approach provides a general strategy for the regeneration of complex injury types.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in surface chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "fluid" refers to a homogeneous or heterogeneous phase that is capable of demonstrating fluidic (flowing) behavior under the experimental conditions under consideration. In certain embodiments, a fluid comprises a liquid, a suspension, a solution or a gas. In other embodiments, the fluid may comprise dissolved chemical compounds, suspended solids and/or suspended cells. In other embodiments, the fluid consists essentially of a liquid or a gas. In yet other embodiments, the fluid consists of a liquid or a gas.

As used herein, the term "instructional material" includes a publication, a recording, a diagram, or any other medium of expression that may be used to communicate the usefulness of the compositions, devices and/or methods of the present invention. In certain embodiments, the instructional material may be part of a kit useful for generating compositions of the present invention. The instructional material of the kit may, for example, be affixed to a container that contains compositions and/or devices of the present invention or be shipped together with a container that contains compositions and/or devices of the present invention. Alternatively, the instructional material may be shipped separately from the container with the intention that the recipient uses the instructional material and compositions, methods and/or devices cooperatively. For example, the instructional material is for use of a kit; or instructions for use of the compositions, methods and/or devices of the present invention.

As used herein, the term "µm" is the abbreviation for "micron" or "micrometer", and it is understood that 1 µm=0.001 mm=$10^{-6}$ m=1 millionth of a meter.

As used herein, the term "nm" is the abbreviation for "nanometer" and it is understood that 1 nm=1 nanometer=$10^{-9}$ m=1 billionth of a meter.

Throughout this disclosure, various aspects of the present invention may be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so on, as well as individual numbers within that range, for example, 1, 2, 2.7, 3, 4, 5, 5.3, and 6. This applies regardless of the breadth of the range.

Disclosure

The present invention provides in certain aspects a novel 3D printing approach for nerve regeneration pathways that are personalized to anatomical geometry. The compositions and methods of the present invention allow for the use of physical and biochemical cues to promote the simultaneous regeneration of multiple nerve pathways. In certain embodiments, the biomimetic nerve conduits of the present invention match the final pathway geometric design to the original tissue structure. In other embodiments, the biomimetic nerve conduits of the present invention incorporate physical and biochemical cues in the form of, respectively, microgrooves and multicomponent diffusive biomolecular gradients.

In certain embodiments, the use of 3D printing to prepare the conduits of the invention allows for the generation of complex geometries that include and go beyond linear cylindrical geometries, which are the only geometries accessible using traditional methods of making conduits. Such complex geometries include, but are not limited to, linear conduits, branched conduits and more complex/customized/patient-specific geometries.

The presently described 3D printing approach allows for generating multi-functional devices. The approach allows for preparing the conduit, as well as introducing physical cues and biochemical cues, using the same printer. In certain embodiments, the compositions of the invention are prepared by extrusion. In contrast, multiphoton polymerization approaches to 3D printing can produce only polymers for the conduits, and cannot introduce physical cues and biochemical cues. Further, the present approach also enables tuning of the physical cue through modulation of the dispensing system parameters.

Compositions

The present invention provides compositions, such as biomimetic nerve conduits, which are exemplified in a non-limiting manner herein. The present invention should not be construed to be limited to the description herein, and contemplates any combination(s) of the embodiments recited herein.

The present invention provides biomimetic nerve conduits comprising a central tube, wherein the central tube comprises a tube wall ("primary tube wall"), which defines and surrounds a lumen within the tube wall ("primary lumen"), and wherein both ends of the central tube are open. In certain embodiments, the conduit of the present invention further comprises at least one branching tube, wherein the at least one branching tube comprises a tube wall ("secondary tube wall"), which defines and surrounds a lumen within the tube wall ("secondary lumen"). The proximal end of the at least one branching tube is physically attached to the central tube wall, and the secondary lumen of the at least one branching tube is in fluid communication with the secondary lumen of the central tube. In other words, the central tube and the at least one branching tube are configured so that there is fluidic flow between the lumen of the central tube and the lumen of the at least one branching tube. In other words, the lumen of the central tube and the lumen of the at least one branching tube are in physical contact, and any material in the primary lumen may penetrate or migrate to the secondary lumen, and vice-versa. Such materials may include in non-limiting examples liquids, solutions, suspensions and/or cells. Further, the distal end of the at least one branching tube is open.

In certain embodiments, the conduit of the present invention comprises one branching tube. In other embodiments, the conduit of the present invention comprises two branching tubes. In yet other embodiments, the conduit of the present invention comprises three branching tubes. In yet other embodiments, the conduit of the present invention comprises four branching tubes. In yet other embodiments, the conduit of the present invention comprises five or more branching tubes. In yet other embodiments, the two or more branching tubes are evenly spaced along the length of the central tube. In yet other embodiments, the two or more branching tubes are not evenly spaced along the length of the central tube.

In certain embodiments, the biomimetic nerve conduit of the present invention has a geometry corresponding to a section of a mammal's nerve pathway. In other words, the conduit has at least one physical dimension (such as, but not limited to, length, thickness, shape, number and/or position of bifurcations, and so forth) that approximates and/or matches that of the nerve pathway. In other embodiments, the biomimetic nerve conduit of the present invention has approximately the same Young's modulus as a mammal's nerve pathway.

In certain embodiments, the central tube has a length ranging from about 0.1 cm to about 100 cm, about 0.1 cm to about 80 cm, about 0.1 cm to about 60 cm, about 0.1 cm to about 40 cm, about 0.1 cm to about 20 cm, about 0.1 cm to about 10 cm, about 0.2 cm to about 10 cm, about 0.3 cm to about 10 cm, about 0.4 cm to about 10 cm, about 0.5 cm to about 10 cm, about 0.6 cm to about 10 cm, about 0.7 cm to about 10 cm, about 0.8 cm to about 10 cm, about 0.9 cm to about 10 cm, about 1 cm to about 10 cm, about 2 cm to about 10 cm, about 3 cm to about 10 cm, about 4 cm to about 10 cm, about 5 cm to about 10 cm, about 6 cm to about 10 cm, about 7 cm to about 10 cm, about 8 cm to about 10 cm, about 9 cm to about 10 cm, and any interval thereinbetween.

In certain embodiments, the at least one branching tube has a length ranging from about 0.1 cm to about 100 cm, about 0.1 cm to about 80 cm, about 0.1 cm to about 60 cm, about 0.1 cm to about 40 cm, about 0.1 cm to about 20 cm, about 0.1 cm to about 10 cm, about 0.2 cm to about 10 cm, about 0.3 cm to about 10 cm, about 0.4 cm to about 10 cm, about 0.5 cm to about 10 cm, about 0.6 cm to about 10 cm, about 0.7 cm to about 10 cm, about 0.8 cm to about 10 cm, about 0.9 cm to about 10 cm, about 1 cm to about 10 cm, about 2 cm to about 10 cm, about 3 cm to about 10 cm, about 4 cm to about 10 cm, about 5 cm to about 10 cm, about 6 cm to about 10 cm, about 7 cm to about 10 cm, about 8 cm to about 10 cm, about 9 cm to about 10 cm, and any interval thereinbetween.

The tube walls of the central tube and the tube wall of the at least one branching tube may be comprised of the same material, or may be comprised of different materials. In certain embodiments, the material used to prepare any of the tube walls is biocompatible and optionally biodegradable. Non-limiting examples of materials contemplated for the preparation of tube walls include one or more synthetic polymers (such but not limited to polylactides, polyglycolids, poly(meth)acrylates, polycarbonates, thiolene based resins, polyvinylchlorides, polytetrafluoroethylenes, polyethersulfones, polyethylenes, polyethretherketones, polysulfones, polypropylenes, polydimethylsiloxane (PDMS), polycaprolactones and silicones) and one or more biopolymers (such as but not limited to alginate, hyaluronic acid, collagen or other extracellular matrix-derived hydrogels).

In certain embodiments, the central tube wall's inner surface comprises a plurality of longitudinally extending indentations (in other words, the indentations are oriented along the longitude of at least a section of the central tube). As contemplated herein, "indentation" refers to a structure that extends below the average surface of the tube wall, such as a lowered detail, a microgroove and/or a microchannel, and/or above the average surface of the tube wall, such as a raised detail or a fiber. In other embodiments, the at least one branching tube wall's inner surface comprises a plurality of longitudinally situated indentations (in other words, the indentations are oriented along the longitude of at least a section of the branching tube). In other embodiments, such indentations along the same tube have approximately the same shape, length, thickness, diameter, height and/or depth. In yet other embodiments, such indentations along the same tube do not have approximately the same shape, length, thickness, diameter, height and/or depth.

In certain aspects, the plurality of longitudinally extending indentations constitute luminal physical cues that are axially oriented. In certain embodiments, the 3D printed nerve pathways of the invention contain an axial physical cue with a microgroove architecture. In other embodiments, these physical cues qualitatively approximate, mimic and/or resemble naturally occurring physical cues present in degraded nerve pathways (known as the bands of Büngner), which guide regenerating axons in vivo. In yet other embodiments, physical cues in the form of microfibers and microgrooves affect the orientations of the two main components of regenerating peripheral nerve: axons and Schwann cells.

In certain embodiments, the primary lumen of the central tube and/or the secondary lumen of the at least one branched tube independently contain(s) a hydrogel. In other embodiments, the primary lumen of the central tube and the secondary lumen of the at least one branched tube independently contain a hydrogel.

The hydrogels contained within each of the tubes of the biomimetic nerve conduit may be approximately the same, or may be different from each other by virtue of differences in the material(s) that form(s) the hydrogel and/or the biologically active agent(s) dispersed/dissolved/suspended therein. In certain embodiments, the hydrogel contained within the lumen of the central tube is different from the hydrogel contained within the lumen of the at least one branching tube. In other embodiments, the hydrogel in each individual tube is independently selected from the group consisting of calcium alginate, agarose, fibrin, collagen, laminin, fibronectin, glycosaminoglycan, hyaluronic acid, heparin sulfate, chondroitin sulfate A, dermatan sulfate, gelatin, bone matrix gelatin, methacrylated gelatin, polyethylene glycol and any mixture therein.

In certain embodiments, the biologically active agent contained in one or more of the tubes of the biomimetic nerve conduit comprises at least one selected from a micro RNA, a single stranded DNA, a double stranded DNA, a cell, a filler, a therapeutic drug, a chemoattractant, a biocide, a peptide, a protein, a chemoattractant, a catalyst and any combinations thereof. In other embodiments, the biologically active agent contained in one or more of the tubes of the biomimetic nerve conduit comprises at least one selected from the group consisting of nerve growth factor (NGF), glial cell line-derived neurotrophic factor (GDNF), and vascular endothelial growth factor (VEGF).

In certain embodiments, the hydrogel in each tube is present as a plurality of droplets. In other embodiments, each one of the plurality of droplets occupies the whole cross section of the lumen where it is located, in other words, "plugs" the lumen at the position where it is located. The plurality of droplets may be positioned within the lumen of the tube in different patterns. In a non-limiting example, the plurality of droplets is added to the lumen of the tube such that the longitudinal spacial separation of successive hydrogel droplets along the tube is uniform. In another non-limiting example, the plurality of droplets is added to the lumen of the tube such that the longitudinal spacial separation of successive hydrogel droplets along the tube is not uniform; for example, the longitudinal spacial separation of successive hydrogel droplets along the tube is such that a gradient of hydrogel droplets along the longitudinal dimension of the tube is formed. In a non-limiting example, the longitudinal spacial separation between consecutive hydrogel droplets along the at least one branching tube is greater near the proximal end than near the distal end. In another non-limiting example, the longitudinal spacial separation between consecutive hydrogel droplets along the at least one branching tube is greater near the distal end than near the near end.

In certain aspects, the hydrogels contain 3D printed biochemical cues, which are displayed in an axial spatiotemporal gradient within each nerve pathway. In certain embodiments, the release of biochemical cues from the hydrogel occurs via a diffusive release mechanism. In a non-limiting example, the longitudinal spacial separation between consecutive hydrogel droplets along the at least one branching tube is greater near the proximal end than near the distal end. This results in an axial gradient within the inside of the nerve pathway, which is concentrated at the distal end and stretches across the full thickness of the guide. The presence of a higher relative concentration of biochemical cue in the distal end of the pathway provides a driving force for the regenerating sensory and motor nerves to re-innervate the proper distal organ pathways.

Methods and Systems

The present invention provides methods and/or systems, which are exemplified in a non-limiting manner herein. The present invention should not be construed to be limited to the description herein, and contemplates any combination(s) of the embodiments recited herein.

The present invention provides methods of promoting nerve regeneration in a mammal in need thereof. In certain embodiments, a section of one of the mammal's nerve pathway is missing or damaged, thus generating at least two severed nerve pathway extremities. In other embodiments, the method comprises physically connecting the at least two severed nerve pathway extremities using any of the biomimetic nerve conduits of the present invention.

In certain embodiments, the biomimetic nerve conduit has a geometry corresponding to the missing or damaged section of the mammal's nerve pathway. In other words, the conduit has at least one physical dimension (such as, but not limited to, length, thickness, shape, number and/or position of bifurcations, and so forth) that approximates and/or matches that of the nerve pathway. In other embodiments, the biomimetic nerve conduit is 3D printed based on a 3D computer model of the missing or damaged section of the mammal's nerve pathway. In yet other embodiments, the 3D computer model is generated by scanning the area where the missing or damaged section of the mammal's nerve pathway is located in the mammal. In yet other embodiments, the 3D computer model is generated by analyzing the nerve pathways of a similar mammal. In yet other embodiments, the biomimetic nerve conduit comprises a motor branch and a sensory branch.

In certain embodiments, the biomimetic nerve conduit is generated using a layer-by-layer fused deposition 3D printing method. In other embodiments, a plurality of longitudinally extending indentations are present along the inner surface of at least one tube wall of the biomimetic nerve conduit. In yet other embodiments, the plurality of longitudinally extending indentations have a microgroove architecture. In yet other embodiments, the plurality of longitudinally extending indentations have a fiber architecture. In yet other embodiments, at least one of the plurality of longitudinally extending indentations has a geometry corresponding to a band of Büngner. In yet other embodiments, at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell. In yet other embodiments, a plurality of droplets are distributed in a spatial relationship along the longitudinal dimension of at least one tube. In yet other embodiments, the plurality of hydrogel droplets contain an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets. In yet other embodiments, the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit.

The present invention further provides a system for producing a subject-specific 3D biomimetic nerve conduit, which is used to replace a missing or damaged section of a nerve pathway of a mammal. In certain embodiments, the system comprises an imaging system configured to generate a 3D image of the missing or damaged section of the nerve pathway of the mammal or a 3D image of the intact nerve pathway of a similar mammal. In other embodiments, the system comprises a modeling system configured to generate a corresponding 3D computer model from the 3D image of the missing or damaged section of the nerve pathway of the mammal or a 3D image of the intact nerve pathway of a similar mammal. In yet other embodiments, the system comprises a 3D printer configured to generate any of the biomimetic nerve conduits of the present invention. In certain embodiments, the biomimetic nerve conduit has a geometry corresponding to the missing or damaged section of the nerve pathway of the mammal. In other embodiments, the biomimetic nerve conduit comprises at least one motor branch and at least one sensory branch. In yet other embodiments, the lumen of at least one selected from the group consisting of the motor branch and the at least one sensory branch independently contains a hydrogel.

The invention further provides a method of producing a 3D subject-specific biomimetic nerve conduit, which is used to replace a missing or damaged section of a nerve pathway of a mammal. In certain embodiments, the method comprises obtaining a 3D image of the missing or damaged section of the nerve pathway of the mammal or a 3D image of the intact nerve pathway of a similar mammal. In other embodiments, the method comprises using the 3D image to print a biomimetic nerve conduit that a geometry corresponding to the missing or damaged section of the mammal's nerve pathway, wherein the biomimetic nerve conduit comprises at least one motor branch and at least one sensory branch. In certain embodiments, the lumen of at least one selected from the group consisting of the at least one motor branch and the at least one sensory branch independently contains a hydrogel.

In certain embodiments, the 3D printer allows for a plurality of longitudinally extending indentations to be present along the inner surface of at least one tube wall of the biomimetic nerve conduit. In other embodiments, the plurality of longitudinally extending indentations have a microgroove architecture. In yet other embodiments, the plurality of longitudinally extending indentations have a fiber architecture. In yet other embodiments, at least one of the plurality of longitudinally extending indentations has a geometry corresponding to a band of Büngner. In yet other embodiments, at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell. In yet other embodiments, the 3D printer allows for a plurality of droplets to be distributed in a spatial relationship along the longitudinal dimension of at least one tube. In yet other embodiments, the plurality of hydrogel droplets contain an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets. In yet other embodiments, the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit.

Every formulation or combination of components described or exemplified can be used to practice the present invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. Although the description herein contains many embodiments, these should not be construed as limiting the scope of the present invention but as merely providing illustrations of some of the presently preferred embodiments of the present invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the present invention.

The following examples further illustrate aspects of the present invention. However, they are in no way a limitation of the teachings or disclosure of the present invention as set forth herein.

EXAMPLES

The present invention is now described with reference to the following Examples. These Examples are provided for the purpose of illustration only, and the present invention is not limited to these Examples, but rather encompasses all variations that are evident as a result of the teachings provided herein.

Materials and Methods

In situ 3D scanning. Imaging of the sciatic nerve bifurcation via structured light scanning (SLS) was done using Sprague-Dawley rats (Hilltop Labs Inc., Pittsburgh, Pa.). For each study, the animal was euthanized, and the sciatic nerve bifurcation was exposed for imaging by making an incision at the base of the gastrocnemius and carefully cutting along the outside edge of the muscle and along the biceps femoris. The muscle was then pulled back to expose the underlying sciatic nerve. A thin film of a scanning contrast agent (Magnaflux) was then applied to the nerve while masking the surrounding tissue to provide enhanced contrast for the nerve during scanning. The contrast agent was later removed with a saline solution wash following scanning Subsequently, a clean low-contrast wound dressing was re-applied around and underneath the exposed nerve, which further enhanced the contrast for the nerve and reduced the signal from the surrounding muscle tissue. The animal was then placed on a motorized stage (CR1/M-Z7E, ThorLabs), which allowed the tissue to be imaged from various vantage points over a full rotational angle. The single camera-projector SLS system (SLS-1, David Vision) was then calibrated according to a vendor-provided protocol. Subsequently, the nerve was imaged by performing multiple scans over a full rotational angle. Scan data was collected without the use of scanning software-associated data smoothing or alignment. The above protocol was repeated multiple times over the course of two months using randomly selected animals (n=4) in order to simulate application in the point-of-care which models inherent patient-to-patient variance.

Ex situ 3D scanning. Similar to the in situ SLS protocol, the sciatic nerve bifurcation was exposed in euthanized Sprague-Dawley rats (n=3) by first making an incision at the base of the gastrocnemius and carefully cutting along the outside edge of the muscle and along the biceps femoris. The muscle was then pulled back to expose the sciatic nerve. Subsequently, the nerve was transected 2 cm proximal and distal to the bifurcation site in strict accordance with good animal practice. The tissue was subsequently fixed by immersion in a room temperature 4% paraformaldehyde (PFA, Affymetrix)-PBS solution for 20 minutes, and blotted dry to begin the moulding-casting process. A resin cast of the fixed nerve was then made from a silicone mould to provide a rigid and anatomically-consistent model for SLS. Prior to scanning, the cast was coated with a thin film of a scanning contrast agent, and the single camera-projector SLS system was calibrated according to a vendor-provided protocol. Subsequently, the nerve cast was mounted vertically on the motorized stage and was imaged by performing multiple scans over a full rotational angle. Scan data was collected without the use of scanning software-associated data smoothing or alignment. For high resolution imaging, scanning was also performed using a single camera-light emitting diode (LED) SLS system (COMET L3D, Steinbichler Optotechnik) The single camera-LED SLS system was calibrated according to a vendor provided protocol. Subsequently, the nerve cast was mounted on a custom goniometer and imaged by performing multiple scans over a full hemispherical angle. Scan data was collected without the use of scanning software-associated data smoothing or alignment.

Figure 9:
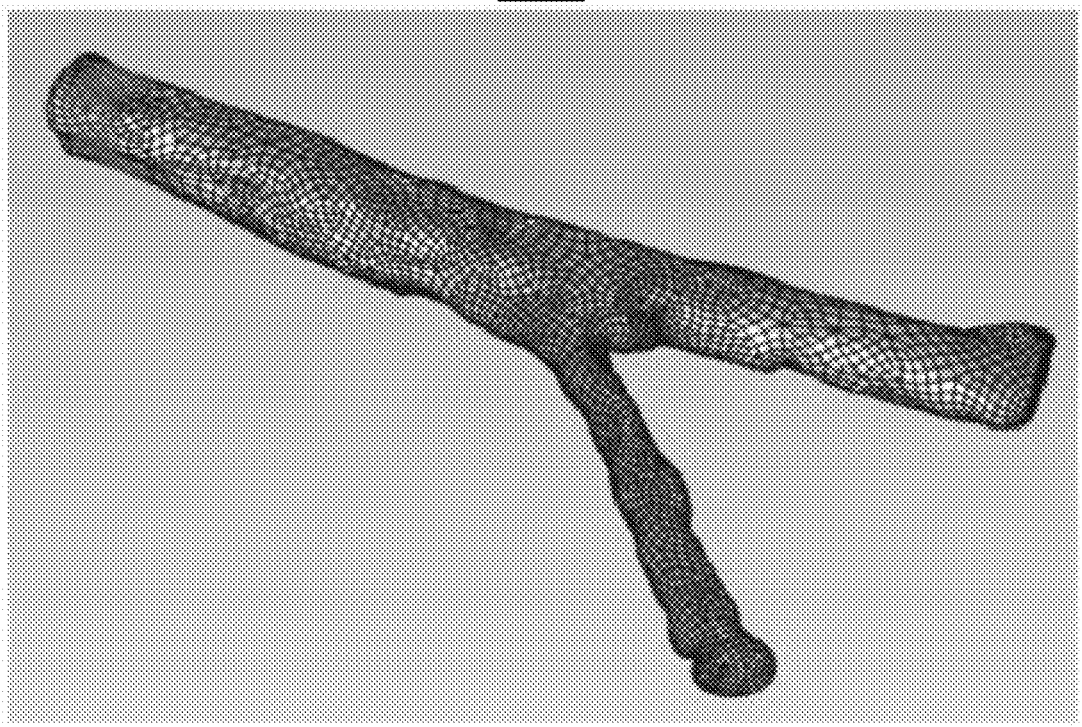
FIG. 9 illustrates non-limiting boundary conditions used for mechanical finite element analysis studies. Blue highlighted elements were restricted to zero displacement condition; tensile and torsional loads were applied to the axial faces of the bifurcated distal end.

Reverse engineering of 3D nerve geometry from scan data. The individual scans obtained using the SLS-1 system were aligned and assembled using 3D mesh processing software (MeshLab) and 3D printing software (Netfabb, FIT GmbH), which resulted in a water-tight 3D model of the imaged nerve. The individual scans obtained using the COMETL3D system were aligned and assembled using reverse engineering software (Geomagic Design X, 3D Systems) and additive manufacturing software (Magics, Materialise) using software-provided alignment and assembly algorithms, which resulted in a water-tight 3D model of the imaged nerve. Finite element analysis of nerve guide solid mechanics. All studies were performed using commercially available finite element analysis (FEA) software (COMSOL Multiphysics, Version 4.4). Stationary studies were conducted in 3D using the Structural Mechanics-Solid Mechanics module. The domain was created by importing the SLS-generated 3D models to the COMSOL modelling environment. All simulations were done assuming a linear elastic material property relationship. The material properties were taken from silicone vendor-provided data (density=1,010 kg/m$^3$), literature values of bulk silicone (Poisson ratio=0.45), and experimental mechanical testing studies conducted on the printed materials (Young's modulus=0.44 MPa). Applied boundary conditions included regions of zero displacement and regions of applied load (FIG. 9). The regions of zero displacement condition served to model constrained regions arising from surgical implantation, while the regions of applied load served to model potential loading conditions that may arise during implantation or post-implantation as a result of mechanical limb motion. Two different loading conditions were examined, which represented tensile or torsional loads. In both cases, a load of 1% of the experimentally measured ultimate tensile strength (UTS) was applied as a basis to demonstrate the value of the approach. The value of UTS was taken from mechanical testing studies conducted on the printed materials, for experiments done with loading applied with the grain, since this printing direction was used for animal studies. Initial values corresponded to zero displacement and velocity fields across the entire domain. The model was discretized using a physics-controlled mesh (normal element size), which consisted of 34,374 domain, 9,982 boundary, and 8,474 edge elements. The von Mises stress profile under both loading conditions was calculated using a stationary solver. Proper density of the mesh was checked by examining convergence of the maximum von Mises stress by iterating from an extremely coarse to a normal mesh element size, which led to convergence within 4-10% of the previous mesh iterate.

Methacrylated gelatin hydrogel synthesis. Gelatin methacrylate was synthesized according to Nichol, et al., 2010, Biomaterials 31:5536-5544. Briefly, a 10% w/v gelatin (porcine skin, Sigma) solution in phosphate buffered saline (PBS) was prepared and heated to 60° C. with constant mixing. After the gelatin was dissolved completely, the temperature was reduced to 50° C. and allowed to reach steady state. After the solution temperature reached 50° C., methacrylic anhydride (Sigma) was slowly added to the solution to achieve a 5:1 volumetric ratio of gelatin solution: methacrylic anhydride solution. The typical basis reaction volume consisted of 50 ml gelatin solution. Subsequently, the mixture was allowed to react for one hour at 50° C. with continual mixing. After one hour, warmed PBS (40° C.) heated in a secondary beaker was added at a 4:1 volume ratio to the gelatin-methacrylic anhydride solution to deactivate the reaction. Subsequently, the resulting mixture was added to 10 kDa dialysis tubing, and the tubing was placed in reverse osmosis water and allowed to dialyze for one week. To ensure effective separation, the dialysis solution was replaced with fresh solution daily. Following the dialysis procedure, the gelatin mixture was lyophilized until dry.

Gelatin hydrogel protein release studies. Controlled drug release studies using 50 mg/ml gelatin hydrogels were done using glial cell line-derived neurotrophic factor (GDNF, Sigma) to characterize the kinetics of the protein release from the gelatin hydrogel matrix. The gelatin hydrogel was prepared on a 1 ml basis containing 400 ng GDNF/ml, 5 mg/ml photoinitiator (Irgacure 2959, BASF), 0.1% bovine serum albumin (BSA) w/w (UltraPure non-acylated, Life Technologies), 1 mg/ml heparin (Sigma), and 0.05% v/v sodium azide (Sigma) in Dulbecco's PBS (DPBS). For drug release measurements, 150 µl of gelatin hydrogel was added to the bottom of a clean containment vessel, cross-linked for 15 minutes using a hand-held UV lamp (UVL-56, UVP) and 600 µl DPBS was added to the vessel. The containment vessel was then sealed and maintained at 37° C. with gentle shaking over the course of a three week period. Multiple identical vessels were prepared to enable collection of samples at various time points over the course of the three week release study. Samples were collected by removing the GDNF containing-DPBS and stored at −4° C. until the end of the study. After three weeks, the level of released protein in the samples was characterized using enzyme-linked immunosorbent assay (ELISA, GDNF mouse ELISA kit, Abcam) according to vendor-provided protocols.

Finite element analysis of nerve guide diffusive biochemical gradient. All studies were performed using commercially available FEA software (COMSOL Multiphysics, Version 4.4). Transient studies were conducted in 2D using the Chemical Species Transport-Transport of Diluted Species module. The domain was created using the software-provided geometry toolbox based on the printed nerve guide and gelatin gradient pattern dimensions. All simulations were done assuming a Fickian transport property relationship. The isotropic protein diffusivity in the gelatin hydrogel system was taken from experimental drug release studies ($3 \times 10^{-13}$ m$^2$/s), and the isotropic protein diffusivity in the aqueous phase was assumed to be $1 \times 10^{-10}$ m$^2$/s. Applied boundary conditions included regions of no flux and regions of flux continuity. The regions with no flux boundary condition served to model the outer edges of the nerve guide, while the regions of flux continuity served to model the interfaces of the gelatin droplets and the surrounding aqueous domain. Applied initial conditions included regions of zero concentration and regions of defined concentration (10 µg/ml), which represented the initially unloaded aqueous and protein-loaded hydrogel domains, respectively. The model was discretized using a physics-controlled mesh (normal element size), which consisted of 3,644 domain and 467 boundary elements. The concentration profile was then calculated using a time-dependent solver. Proper density of the mesh was checked by examining convergence of the steady state concentration by iterating from an extremely coarse to a normal mesh element size, which led to convergence within 0.2% of the previous mesh iterate.

3D printing of bifurcated nerve pathways. Water-tight 3D models of the sciatic nerve bifurcation were imported to 3D printing software (Netfabb, FIT GmbH) and residual errors were repaired. The repaired models were subsequently exported to commercially available 3D CAD design software (SolidWorks) for final optimization. Resultant models were then validated using a commercially available plastic 3D printer (Dimension Elite, Alleghaney Ed. Systems).

Following validation, the 3D models were converted to printer path information using model slicer software (KISSlicer).

Devices were printed using a custom microextrusion-based 3D printing system (Kong, et al., 2014, Nano Lett. 14:7017-7023). Briefly, Briefly, in an exemplary manner, an industrial robotic dispenser (Fisnar, Wayne, N.J.) was modified into a multi-head 3D printer, where up to four different inks can be loaded and independently controlled with an external I/O card and pressure regulators. The printer supports standard size syringe barrels, and universal luer-lock needles. Tips from 27 to 33 gauge (GA) were used depending on the material viscosity and resolution required. For high precision printing, the barrel pressure was regulated from 0 to 100 psi with a digital pressure regulator (Nordson Corporation, Westlake, Ohio). Vacuum suction control of the regulator was used to prevent dripping of low viscosity fluids. Higher viscosity inks were independently regulated with analog pressure regulators (Fisnar, Wayne, N.J.) for multi-material printing. The distance registration was calibrated with a digital CMOS laser sensor (Keyence, Itasca, Ill.), and the printer stage has a maximum resolution of 1 µm per axis. Control of the 3D printer was achieved via custom-written LabVIEW programs through serial connection. Commercially available CAD software, Solidworks Premium 2014 (Dassault Systemes, Velizy-Villacoublay Cedex, France) was used for all modeling applications. The typical printing strategy involved the formatting of 3D CAD files into stereolithography (STL) format, followed by slicing the model into G-code coordinates. The G-code was then translated to the command language of the robotic dispenser via a custom-written LabVIEW program. In some instances, a Peltier stage heater was used and the temperature was modulated with the applied voltage to optimize the printing condition or for annealing the printed film. A UV laser (405 nm) was also integrated to the printer arm to provide curing of photoactive materials, such as the UV adhesive.

Silicone (Superflex Clear RTV, Loctite) and gelatin hydrogel served as exemplary printed materials. For fabrication of devices with luminal path-specific gradients of nerve growth factor (NGF, mouse, Life Technologies) and glial cell line-derived neurotrophic factor (GDNF, mouse, Sigma), methacrylated gelatin hydrogel containing either NGF or GDNF served as the printed luminal supplement. Hydrogel preparation was consistent with drug release studies, except for the azide component, which was removed, and the protein concentration, which was increased to 10 µg/ml. The heparin component was also incorporated into both hydrogels, which acted to both stabilize the protein and inhibit binding of the growth factor to the channel walls. For printing the luminal gradient functionalized devices, the gradient pattern corresponded to hydrogel droplets spaced at sequentially increasing gap sizes of n×100 µm, where n represents the droplet number starting at the distal end of the pathway. This sequentially increasing spacing was truncated at 700 µm, after which constant 1 mm spacing was employed. NGF-loaded hydrogel was printed along the bottom luminal wall of the sensory pathway, and GDNF-loaded hydrogel was printed along the bottom luminal wall of the motor pathway. Subsequent to the hydrogel printing, the hydrogel was partially cross-linked by a UV irradiation period (5 minutes; UVL-56, UVP). Following completion of the silicone printing process, the printed devices were irradiated with UV for an additional period (15 minutes) and sprayed with ethanol to complete crosslinking and sterilization.

Mechanical testing of the 3D printed material anisotropy. In order to examine the effect of the physical cue orientation on the nerve guide mechanical properties, mechanical testing was done on 3D printed silicone samples containing different orientations of the physical cue. Flat rectangular silicone samples were printed with identical layer spacing as used for the surgically implanted 3D printed nerve guides (150 µm), allowed to completely cure at room temperature, and subsequently diced into consistently sized samples. Tensile tests were performed using a commercially available mechanical testing unit (Instron 5865 with Instron 3111 temperature-controlled chamber, 1 kN load cell) under a constant strain rate of 2 in/min. Prior to all tests, the load was reset and the load cell was calibrated. Multiple 3D printed samples were characterized allowing the stress-strain characteristics to be measured with the tensile load applied both with (n=8) and against the grain (n=4) of the 3D printed material. The Young's modulus was taken as the slope of the linear region of the stress-strain curve. The ultimate tensile strength (UTS) was taken as the maximum stress reached before failure. Analysis of the statistical significance in the difference of the UTS between the two groups was done using a two-tailed student t-test.

Characterization of the 3D printed physical cue morphology. Printed nerve pathways were fabricated and subsequently diced into thirds along either the circumference or the length for profilometry and environmental scanning electron microscopy (ESEM) measurements, respectively. The axially-diced samples (n=8) were anchored to SEM specimen mounts using double-sided carbon tape and coated with a thin gold layer for imaging. All measurements were done using a commercially available ESEM platform (FEI Quanta 200). The circumferentially-diced samples (n=4) were mounted on a glass slide using double-sided carbon tape, with the luminal surface facing up. All measurements were done using a commercially available surface profiler (KLA-Tencor P-15).

Cell culture. Primary embryonic sensory neurons were obtained from Sprague-Dawley rats (embryonic day 15.5-16.5). Superior cervical ganglia (SCG) and dorsal root ganglia (DRG) were first harvested. Ganglia were then either maintained in whole form or dissociated (Curanović, et al., in Current Protocols in Cell Biology 26.24.21-26.24.23 (John Wiley & Sons, Inc., 2009); Ch'ng & Enquist, 2005, J. Virol. 79:10875-10889). Briefly, whole ganglia were suspended in 1 ml trypsin (Life Technologies) in a 15 ml conical centrifuge tube and incubated at 37° C. for 15 minutes. The solution was then centrifuged at 1 krcf for 1 min to pellet the ganglia, the supernatant was removed, and the ganglia were resuspended in soybean trypsin inhibitor (2 mg/ml in neurobasal media; Sigma) for 10 min. The solution was then centrifuged, the supernatant was removed, and the ganglia were resuspended in warm growth medium which consisted of neurobasal medium (Life Technologies) containing B-27 medium supplement (Life Technologies), 1% Pen Strep Glutamine (Life Technologies), and nerve growth factor 2.5S (NGF, 100 ng/ml, mouse, Life Technologies). The medium was filtered using a 0.22 µm filter prior to addition of NGF (Stericup filter unit, Millipore). The ganglia were dissociated by repeated aspiration using a flame-polished pipette. Whole ganglia could be stored up to one week in Hibernate-E reagent (Life Technologies). Culture surfaces were pre-coated with poly-L-ornithine (500 µg/ml, Sigma) overnight at 37° C., rinsed 3 times with DPBS, coated in laminin (10 µg/ml, Sigma) overnight at 37° C., and rinsed 3 times with DPBS. Whole DRG or dissociated SCG were seeded with an inoculum 1-3 DRG or SCG/35 mm dish and cultured at 37° C. and 5% $CO_2$ in complete growth medium. Antimitotic agent cytosine arabinoside (AraC, Sigma) was added to the medium 2 days after plating to inhibit fibroblast outgrowth. Two-thirds of medium was exchanged every 7-10 days.

Schwann cells derived from rat sciatic nerves were purchased from a culture collection organization (S16, CRL-2941, ATCC). Culture surfaces were pre-coated with poly-L-lysine (0.1 ml/cm$^2$ surface area with a 15 µg/ml solution, Sigma) overnight at 37° C., rinsed 3 times with DPBS, and allowed to dry for a minimum of 30 minutes at room temperature. Schwann cells were then seeded with an average inoculum of $4\times10^3$ to $6\times10^4$ cells/cm$^2$ and cultivated over 5-7 days at 37° C. and 5% $CO_2$ in Dulbecco's modified Eagles medium (DMEM, Life Technologies) containing 10% fetal bovine serum (FBS, Life Technologies) and 1% Pen Strep (Life Technologies). The medium was filtered using a 0.22 µm filter. Two-thirds of medium was exchanged every 2-3 days.

Immunofluorescence. Following cultivation, cells were fixed in a PFA solution (4% in PBS, Electron Microscopy Sciences) for 20 minutes at room temperature, rinsed with DPBS, permeabilized in a Triton X-100 solution (0.1% in PBS, Sigma) for 30 min at room temperature, rinsed with DPBS, and blocked with a BSA solution (3% in PBS, Sigma) overnight at 4° C. Subsequently, the BSA solution was removed and the cells were stained using primary antibodies. Axons were stained for Tau marker using anti-Tau (1:1000 in diluted blocking solution, monoclonal, mouse, Life Technologies) overnight at 4° C. Schwann cells were stained for glial fibrillary associated protein (GFAP) and laminin markers using anti-GFAP (1:1000 in diluted blocking solution, monoclonal, mouse, Sigma) and anti-laminin (1:1000 in diluted blocking solution, polyclonal, rabbit, Sigma) overnight at 4° C., respectively. Subsequently, the samples were rinsed 3 times in DPBS and exposed to labelled secondary antibody against mouse (1:1000 in diluted blocking solution, Alexa Flour 488 anti-mouse, Life Technologies) and rabbit (1:1000 in diluted blocking solution, Alexa Flour 568 anti-rabbit, Life Technologies) overnight at 4° C. Following secondary antibody labelling, the samples were rinsed 3 times in DPBS and coated with a thin layer of mountant (ProLong Gold Antifade with DAPI, Life Technologies). Imaging was then carried out using a fluorescence microscope (Nikon Eclipse 50i, X-Cite 120 Fluorescence Illumination Source [EXFO]).

Characterization of the 3D printed physical cue on neurite network orientation. Circumferentially-diced 3D printed nerve pathways were anchored at the well bottom in uncoated 35 mm dishes using a silicone adhesive layer with the luminal surface facing up and subsequently allowed to cure overnight. The exposed luminal surface was then pre-coated, and whole DRG or dissociated SCG were seeded, cultivated for 3 weeks, and the cultures were then imaged. Similar experiments were done in the 3D printed bifurcating nerve pathways, in which the printing was interrupted halfway through the program, resulting in an open half-shell geometry. The devices were then pre-coated, whole DRG were seeded near the center of the bifurcation point, cultivated over a 3 week period, and the cultures were then imaged. A minimum amount of medium was added such that the liquid height just reached the top of the silicone pathway (2 ml). The images were then processed so that the printed physical cue was oriented horizontally across the image providing a basis for the printed physical cue orientation at 90°. The orientation of neurite network was then examined using ImageJ software. Images were processed using a fast Fourier transform (FFT) and resultant power spectrums were then generated by plotting the FFT signal intensity along a circumferential profile.

Characterization of the 3D printed physical cue effect on schwann cell orientation. Circumferentially-diced 3D printed nerve pathways were anchored at the well bottom in uncoated 6-well plates using a silicone adhesive layer with the luminal surface facing up and subsequently allowed to cure overnight. The exposed luminal surface was then pre-coated, Schwann cells were seeded, cultivated over 5-7 days, and the cultures were then imaged. The images were then processed so that the printed physical cue was oriented horizontally across the image providing a basis for the printed physical cue orientation at 90°. The orientation of Schwann cell structure was then examined using ImageJ software. Images were processed using a FFT and resultant power spectrums were then generated by plotting the FFT signal intensity along a circumferential profile.

Characterization of the GDNF gradient effect on schwann cell migration. Individual wells of 6-well plates were first pre-coated. Following the pre-coating steps, one sterile 3D printed silicone compartmented neural chamber was placed in each well to form a seal along the bottom of the well. Schwann cells were then seeded in the middle compartment and allowed to settle overnight under growth conditions. The medium was aspirated and the silicone compartment was peeled off, resulting in seeded cells concentrated in a rectangular configuration at the center of the well. Subsequently, 50 µl of GDNF-containing gelatin hydrogel (1 µg/ml) were added along the edge of the well, the seeded cells were masked, and the hydrogel was crosslinked with UV irradiation for 10 minutes. The mask was then removed, 1 ml of fresh warm medium was added to the well, and the culture was returned to growth conditions for 2 days to establish the diffusive gradient. Live imaging was done the following day using an inverted phase contrast microscope (Nikon Eclipse TS100) and a live cell perfusion chamber (Quorum Technologies) at 37° C. and 5% $CO_2$. Time-lapse videos captured by recording sequential phase-contrast micrographs at the cell-free surface interface at five minute intervals over a 2 hr period facilitated calculation of the migration velocity, which was defined as the horizontal distance travelled divided by the time interval. The population average migration velocity was calculated by averaging the migration velocity of the leading cells (n=8-12) along the imaged interface. Control studies were done by carrying out repeated experiments, which lacked the diffusive GDNF gradient. Analysis of the statistical significance in difference of the migration velocity between the two groups was done using a two-tailed student t-test.

Characterization of the NGF gradient effect on neurite outgrowth. 35 mm dishes were first pre-coated. Subsequently, 10 µl of NGF-containing gelatin hydrogel (1 µg/ml) was added along the edge of the dish, and the hydrogel was cross-linked with UV irradiation for 10 min. Whole DRG were then seeded near the center of the dish, cultivated over a 1 week period, and the cultures were then imaged. Similar experiments were done in the 3D printed bifurcating nerve pathways in which the printing was interrupted halfway through the program resulting in open half-shell geometry. The devices were first pre-coated. Subsequently, 10 µl of hydrogel was added to the distal end of the left path, and UV cross-linked for 10 minutes. Whole DRG were then seeded near the center of the bifurcation point, cultivated over a 3 week period, and the cultures were imaged. A minimum amount of medium was added such that the liquid height just reached the top of the silicone pathway (2 ml). For experiments done in 35 mm dishes lacking the silicone pathway, the hydrogel source was oriented to the right of the captured image for subsequent analysis. The orientation of the neurite network was then characterized using ImageJ software by counting the number of axon bundles growing towards the source (referred to as up the gradient) and away from the source (referred to as down the gradient). The fraction of axon outgrowth was calculated as the number of directionally growing axon bundles divided by the total number of bundles. Control studies were done by carrying out repeated experiments which lacked the diffusive NGF gradient. Analysis of the statistical significance in difference of the axon outgrowth between the two groups was done using a two-tailed student t-test.

Sciatic nerve transection and repair model. Male Wistar rats (300-350 g, Charles River) were used in this study. All animals (n=3) were maintained in the Animal Facility of the University of Maryland School of Medicine. Both limbs underwent sciatic nerve transection. The right limb was randomly selected to be repaired with the bifurcated nerve guides, which contained no added biochemical functionality, and the left limb was repaired with bifurcated nerve guides which contained path-specific gradients of NGF and GDNF in the respective sensory and motor channels. Sciatic nerve transection and repair were done as described in Lewitus, et al., 2011, IEEE Trans. Neural Syst. Rehabil. Eng. 19:204-212. Prior to implantation, the nerve guides were sterilized via ethylene oxide treatment. Briefly, 1 cm of the sciatic nerve was transected 0.5 cm both proximal and distal to the bifurcation point of the sciatic nerve. The epineurium of all nerve stumps was sutured to the nerve scaffold four times on each side using 9-0 sutures under a microscope. The proximal channel was sutured to the sciatic nerve, the distal sensory channel was sutured to the sural nerve, and the distal motor channel was sutured to the tibial nerve motor braches to the gastrocnemius muscle. The muscular and skin incisions were then closed in layers. The animals had free access to food and water before and after the experiments, and were subjected to a 12 hr day/night cycle in a quiet environment.

Gait analysis. Automated gait analysis was performed 12 weeks after surgery using a CatWalk system (Noldus). All experiments were performed during the same period of the day (1-4 p.m.) and analyzed as described in Zhen, et al., 2013, Nat. Med. 19:704-712. Briefly, rats were trained to cross the CatWalk walkway daily for 7 days before the surgery. During the test, each rat was placed individually in the CatWalk walkway, which consists of a glass plate (100 cm×15 cm×0.6 cm), plus two Plexiglas walls. The rat was allowed to walk freely and traverse from one side to the other of the walkway glass plate. Two infrared light beams spaced 90 cm apart were used to detect the arrival of the rat and control the start and end of data acquisition. The recordings were carried out when the room was completely dark, with the exception of the light from the computer screen. An LED light from an encased fluorescent lamp was emitted inside the glass plate and completely internally reflected. When the rat paws made contact with the glass plate, light was reflected down and the illuminated contact area was recorded with a high-speed colour video camera positioned underneath the glass plate connected to a computer running Catwalk software v10.5 (Noldus). Comparison was made between the ipsilateral (left) and the contralateral (right) hind paw in each run of each animal at each time point. The duty cycle is defined as the ratio of stand time divided by the sum of stand and swing time (=Stand/[Stand+Swing]). Stand time is the duration of time that the paw is in contact with the glass, and swing time is the duration time that the paw is not in contact with the glass. The comparison of catwalk data between two groups was performed using a paired t-test.

Example 1: 3D Printing Based Customized Nerve Pathway Regeneration

Conventional nerve guidance channels are typically fabricated around cylindrical substrates, so the resultant devices are inherently restricted to linear structures lacking programmable biofunctionality. In certain embodiments, it is desirable to develop strategies that both allow for the reconstruction of pathways with complex anatomical structures and provide internal biofunctionalization.

Figure 1B:
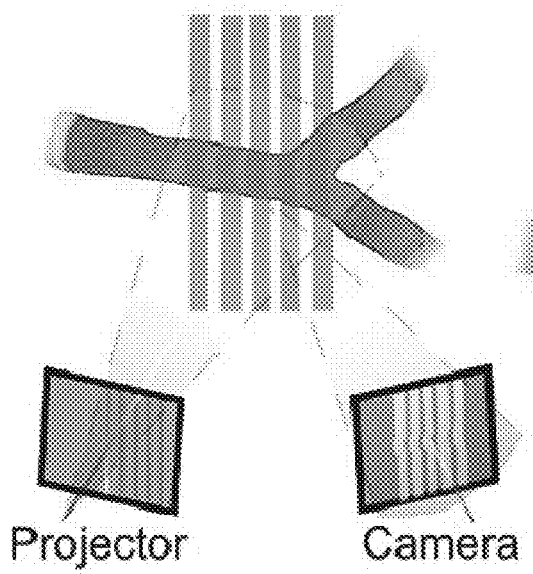
Figure 1C:
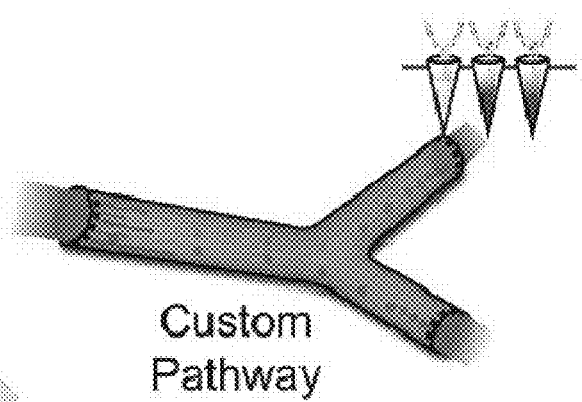

An exemplary strategy to accomplish this goal in a one-pot 3D printing process is illustrated in FIG. 1. The approach encompasses at least three steps: accessing the nerve pathway for imaging, and transecting the bifurcating nerve, which comprises motor and sensory nerve branches from a mixed nerve source (FIG. 1A); imaging the original nerve structure either in situ or ex situ to generate a corresponding 3D computer model (FIG. 1B); and 3D printing a geometrically matching network of pathways that are functionalized with physical cues and path-specific biochemical gradients (FIG. 1C). This approach provides a mechanism for regenerating a damaged nerve plexus, a task that is difficult to accomplish using conventional nerve guidance channels. The sciatic nerve bifurcation was selected as an exemplary tissue model for regeneration, as it contains a mixed nerve system that bifurcates into different sensory (sural) and motor (tibial-peroneal) paths.

Example 2: Reverse Engineering of Nerve Pathway Structure Via 3D Scanning

Figure 2A:
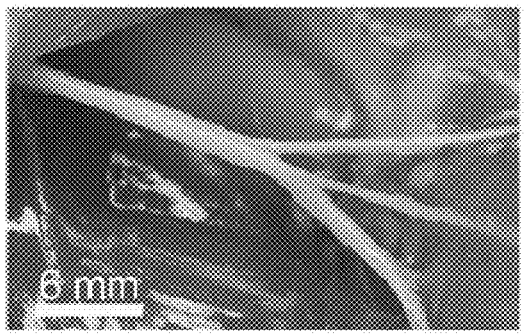
FIGS. 2A-2F illustrate non-limiting 3D printed complex nerve pathways from 3D scanned bifurcating nerves.
Figure 2B:
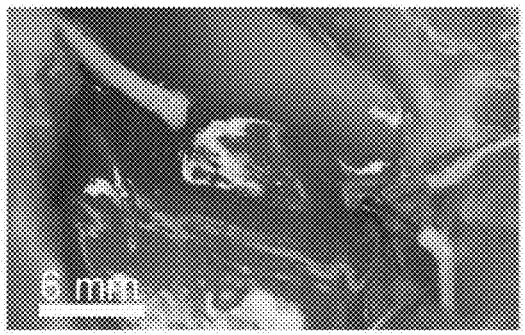
Figure 2C:
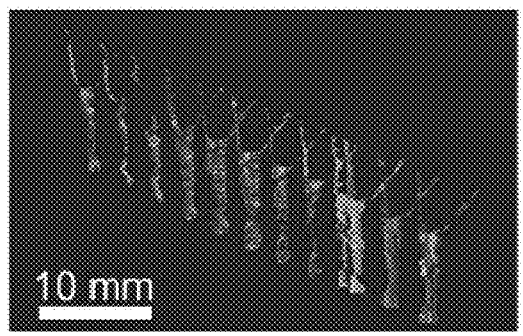
Figure 2D:
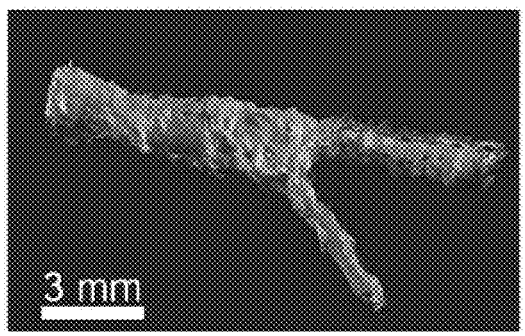

As illustrated in FIG. 2A, the sciatic nerve bifurcates into two distinct sensory and motor paths, which become the sural and tibial-peroneal nerves, respectively. Following exposure of the bifurcating nerve via an incision in the superior muscle tissue, the sciatic nerve was transected above and below the bifurcation point (FIG. 2B). Having selected the bifurcating mixed nerve pathway as a model and acquired the representative tissue sample, a cast of the nerve was then prepared and subsequently imaged using a 3D structured light scanning (SLS) technique. SLS is a valuable imaging technique for reverse engineering of geometrically complex free-form objects, including body parts and teeth, but to date has not been applied towards imaging of internal tissues. As illustrated in FIG. 2C, the SLS technique couples well with tissue cast imaging, ultimately generating multiple data sets that collectively describe the 3D geometry of the imaged nerve model. Following scanning of the cast from multiple perspectives, the individual scans were aligned into a full 3D reconstruction of the original nerve pathway (FIG. 2D), indicating that SLS can be used to accurately reverse engineer the structure of internal tissues.

Figure 2E:
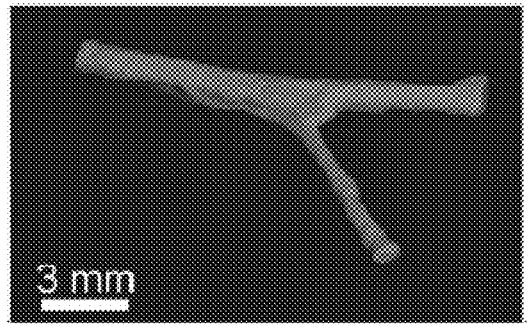
Figure 2F:
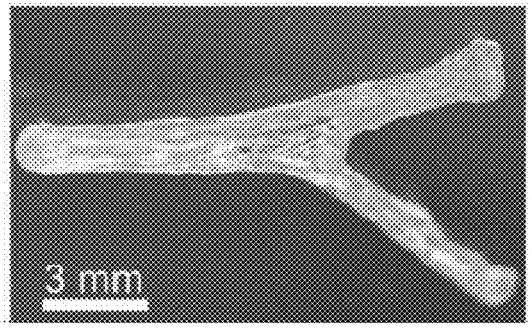
Figure 7A:
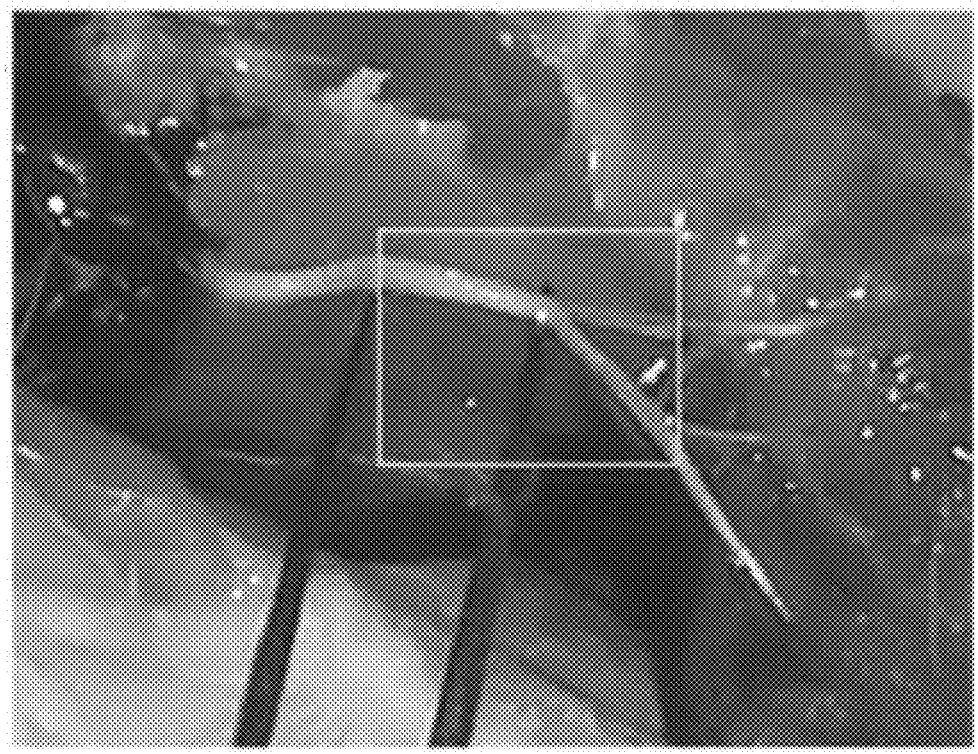
FIGS. 7A-7B illustrate non-limiting scanning data obtained from intact tissue prior to transection.
Figure 7B:
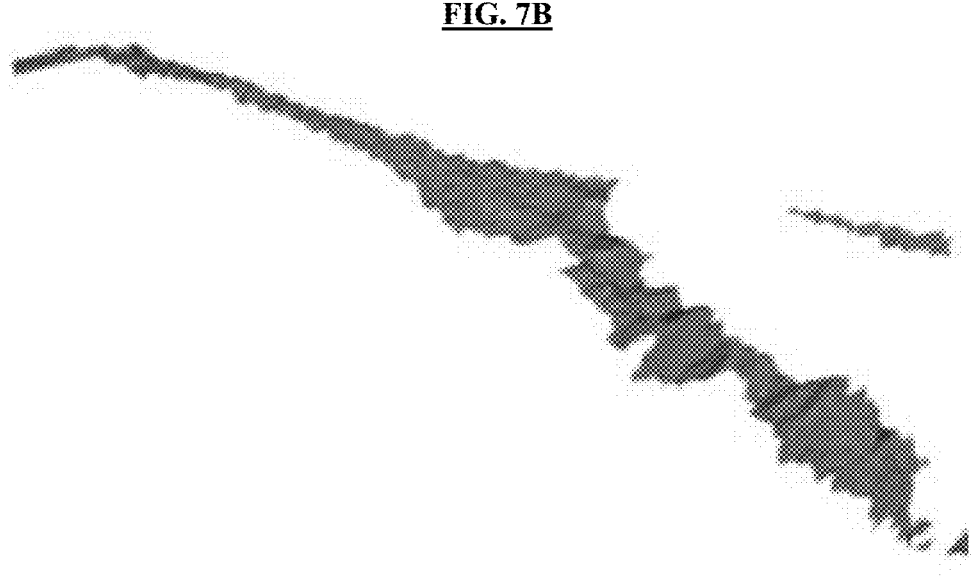

As illustrated in FIG. 2E, the reconstructed 3D model was used to directly manufacture an anatomically accurate nerve pathway for regeneration of the complex nerve gap by using the scanned model as a template for generating 3D printer path information (FIG. 2F). As a non-limiting example, silicone was selected as the guide material due to its widespread use in conduit-based peripheral nerve regeneration applications. As SLS is a highly sensitive imaging technology, studies were conducted to determine whether in situ tissue imaging could be performed without the use of a cadaver model, which would potentially enable point-ofcare applications of the present strategy. As illustrated in FIG. 7, SLS can be used to acquire 3D information of nerve pathways in situ. In certain non-limiting embodiments, the present process is compatible with conventional imaging technologies, such as computed tomography and magnetic resonance imaging.

Example 3: Computational and Mechanical Analysis and Optimization

Figure 3A:
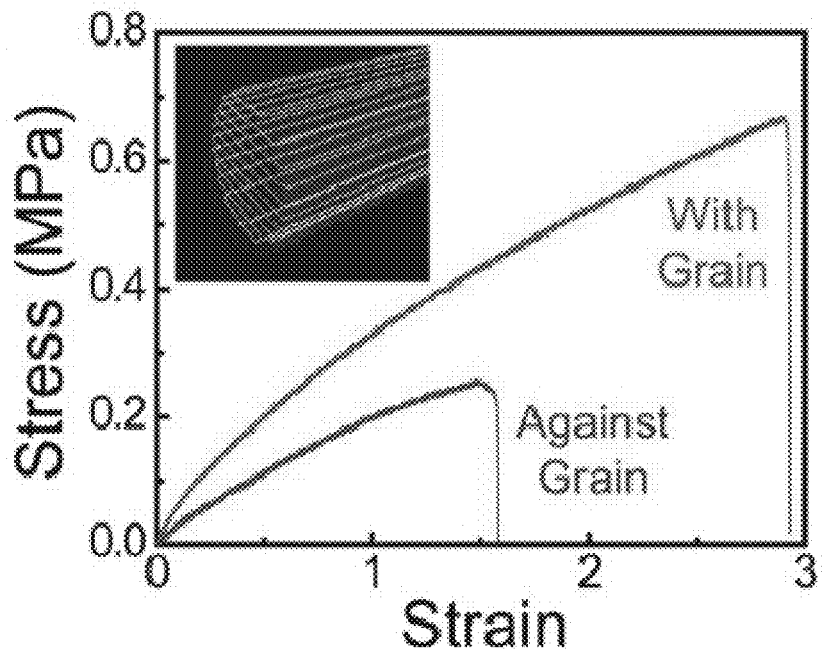
FIGS. 3A-3C illustrate non-limiting mechanical characterization and computational analysis of the pathways.

Mechanical and computational studies afford the opportunity to analyze and optimize the structural integrity of the 3D printed nerve pathways. The mechanical properties of the 3D printed silicone were examined to obtain fundamental parameters and determine the effect of the printing orientation on the mechanical response. As illustrated in FIG. 3A, the 3D computer template of the nerve pathway was first sliced into discrete layers to generate path information for the printer, which creates an inherent grain in the sliced structure due to printing artifacts. For instance, the inset of FIG. 3A shows the grain orientation resulting from slicing in the radial dimension (in contrast to slicing in the axial dimension). The effect of this grain orientation on the mechanical response of the material was tested using tensile strength measurements, in which the tensile load was applied either with or against the grain. As illustrated in FIG. 3A, the samples exhibited linear strain behavior up to 8% strain. At low strain, the 3D printed material resembles the performance of the bulk material, regardless of the grain orientation. The Young's modulus was calculated to be 0.44 MPa, which compares favorably with modulus for bulk silicone and peripheral nerve (0.45 MPa). Without wishing to be limited by any theory, this characteristic helps maintain elastic continuity between the nerve guide and the repaired tissue.

Since material defects are often pronounced at high strains, where nonlinear material behavior occurs, the effect of the 3D printed grain orientation on the ultimate tensile strength (UTS) was also examined. As illustrated in FIG. 3A, the 3D printed material contains anisotropy with respect to its high strain response and ultimate properties. The UTS was significantly higher when the load was applied with the grain than when the load was applied against the grain (0.57 MPa compared with 0.25 MPa, respectively, $p<0.05$).

Figure 8A:
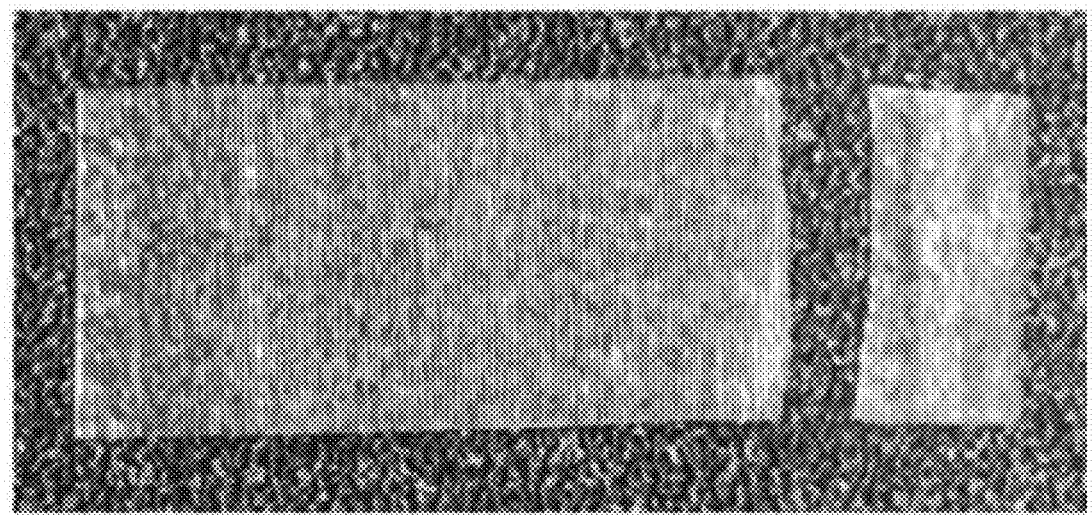
FIGS. 8A-8B illustrate non-limiting mechanical failure mode observed during tensile strength measurements under various grain orientations of the printed material.
Figure 8B:
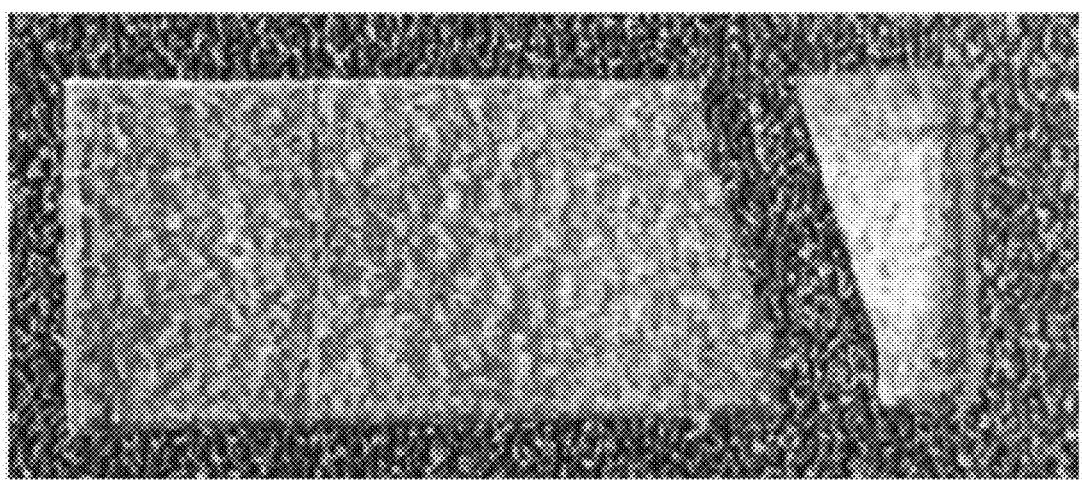

A difference in the failure mechanism of the samples was observed: a tear in the case of the load applied against the grain, in contrast to a relatively rapid snap in the case of the load applied with the grain (FIG. 8). In one aspect, these results suggest that the 3D printed device performs similarly to an equivalent device of bulk silicone with respect to loads applied with the grain, but would be relatively weaker to loads applied against the grain. Since axial loads on the implanted nerve pathways are expected to dominate over radial loads, the guides were printed based on path information generated from slicing the model in the radial dimension, which would result in primary loading with the grain. As a result, the material properties obtained from measurements in which the load was applied with the grain were used in subsequent finite element analysis (FEA) of nerve pathway mechanics.

Figure 3B:
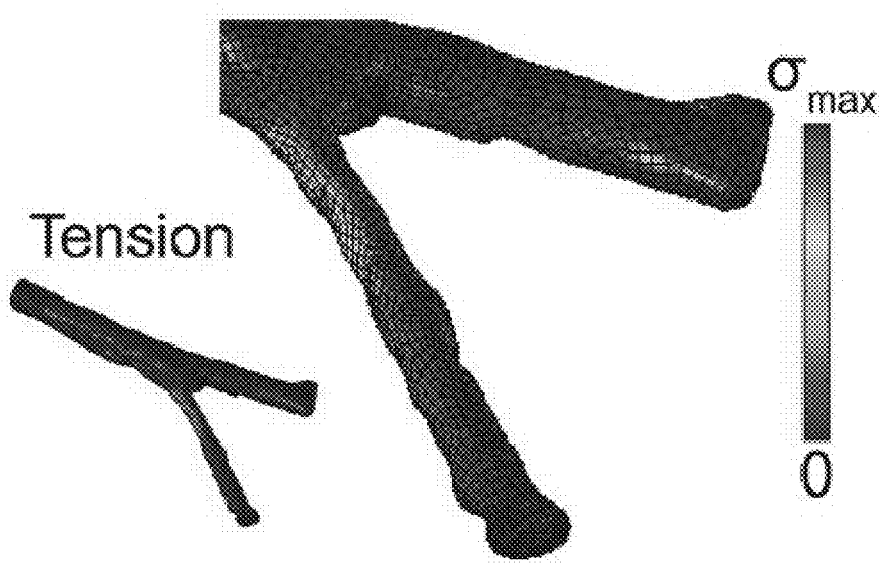
Figure 3C:
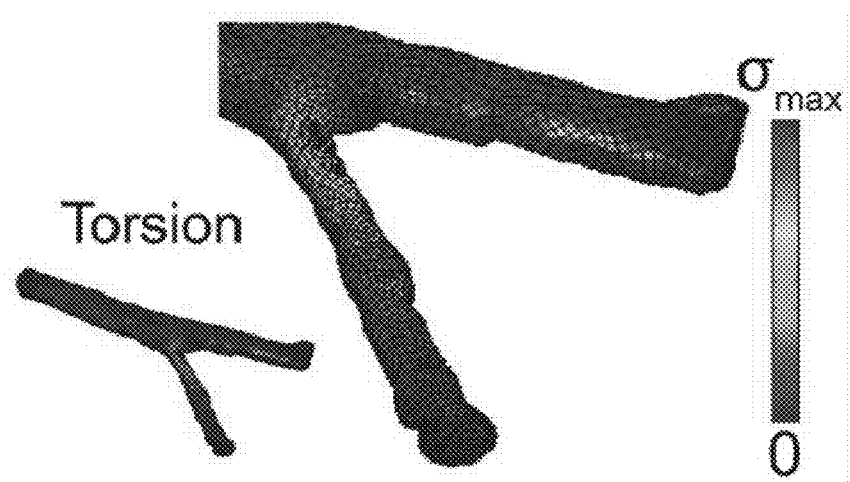

FEA was conducted on the nerve pathway under both tensile and torsional loading conditions (FIGS. 3B-3C, respectively), which occur during both the surgical implantation step and the subsequent regeneration period in vivo. Applied boundary conditions included regions of zero displacement and regions of applied load (FIG. 9). As shown in FIGS. 3B-3C, both loading conditions generated concentrated stress regions near the bifurcation point. In certain embodiments, this information enables one to determine if complex loading conditions cause the nerve pathway to fail, which would obviously compromise the resultant regeneration process. In other embodiments, this information enables one to identify device regions that undergo significant mechanical deformations, which is important since mechanical effects affect axonal growth.

Figure 4A:
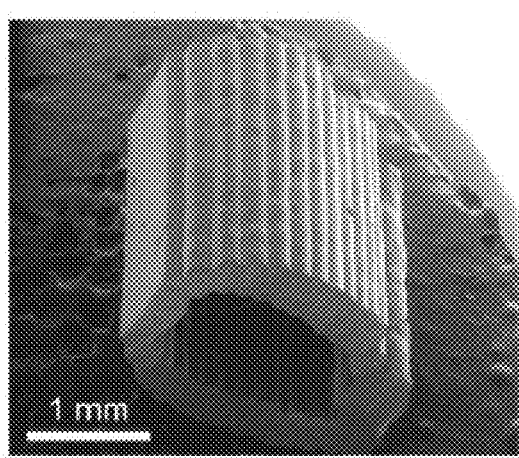
FIGS. 4A-4F illustrate non-limiting characterization and influence of the 3D printed physical cue.
Figure 4B:
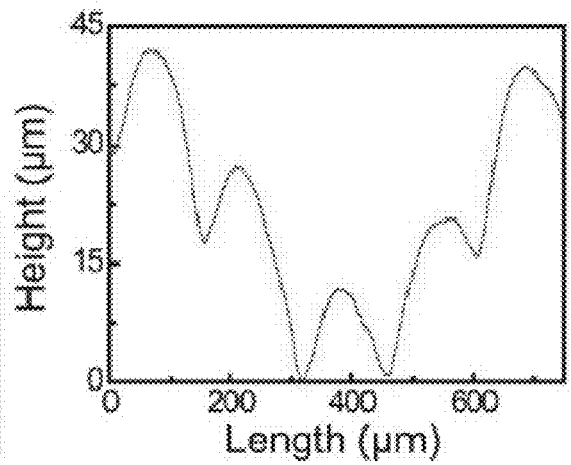
Figure 10:
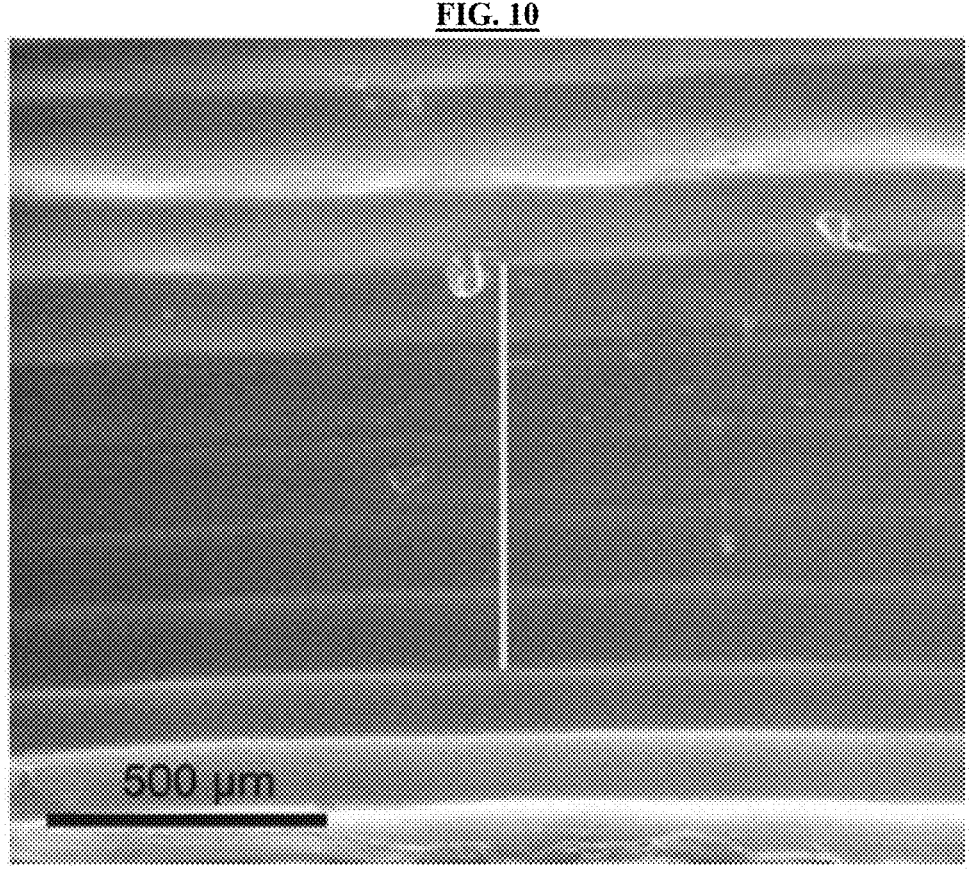
FIG. 10 illustrates non-limiting scanning electron micrograph of the nerve regeneration pathway luminal surface. The image displays the profiled luminal surface corresponding to the profilometry measurement shown in FIG. 4B. The yellow line indicates the path of the surface profiler.
Figure 11A:
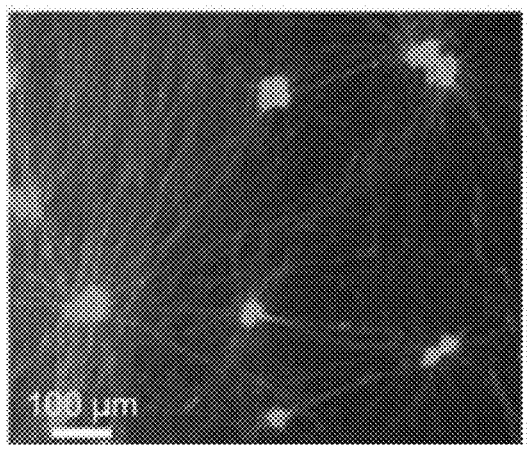
FIGS. 11A-11D illustrate non-limiting analysis of the orientations of the neurite networks and Schwann cell structures from control studies done in the absence of the 3D printed physical cue. Neurite network structure (FIG. 11A) and corresponding orientation analysis (FIG. 11B) in the absence of the 3D printed physical cue. Schwann cell structure (FIG. 11C) and corresponding orientation analysis (FIG. 11D) in the absence of the 3D printed physical cue.
Figure 11B:
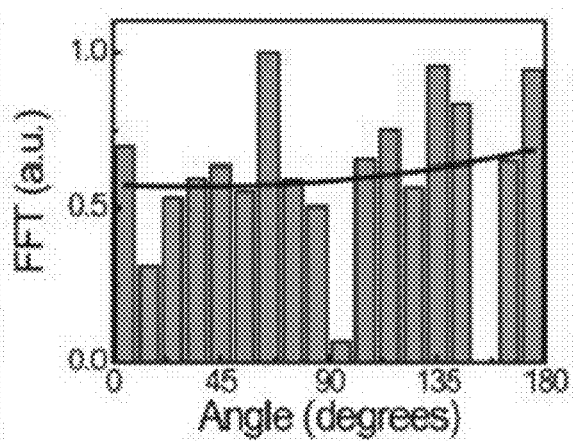
Figure 11C:
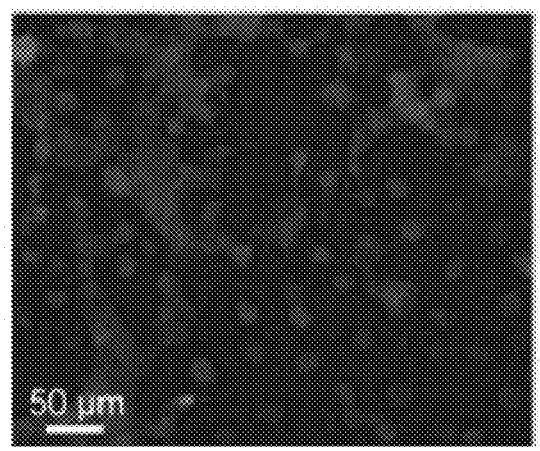
Figure 11D:
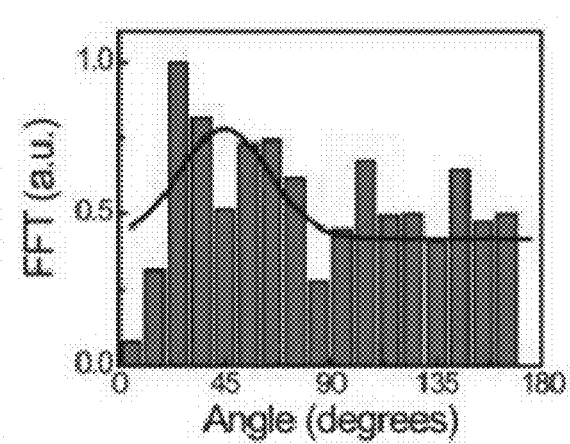

Example 4: Augmentation of Nerve Pathway Functionality with a Biomimetic Physical Cue In addition to providing a material grain that can be rationally selected to optimize the mechanical performance of the nerve pathway, the layer-by-layer fused deposition 3D printing approach also generates a luminal physical cue that is axially-oriented due to model slicing in the radial dimension (FIG. 4A). As illustrated in FIG. 4B, measurement of the luminal surface profile perpendicular to the physical cue orientation reveals that the 3D printed nerve pathways contain an axial physical cue with a microgroove architecture (FIG. 10). This physical cue qualitatively resembles naturally occurring physical cues present in degraded nerve pathways (known as the bands of Büngner), which guide regenerating axons in vivo. Physical cues in the form of microfibers and microgrooves affect the orientations of the two main components of regenerating peripheral nerve, axons and Schwann cells.

Figure 4C:
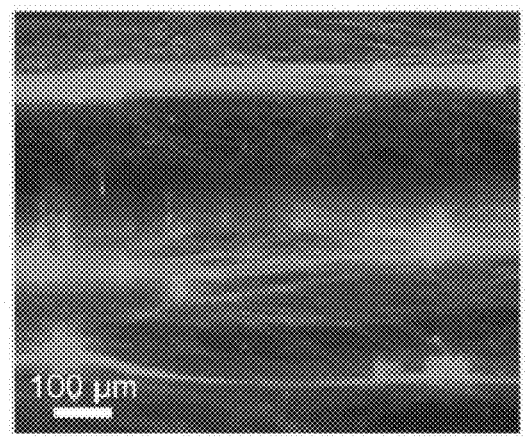
Figure 4D:
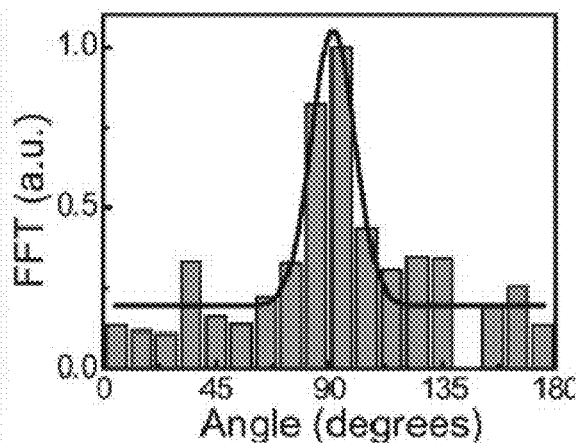
Figure 4E:
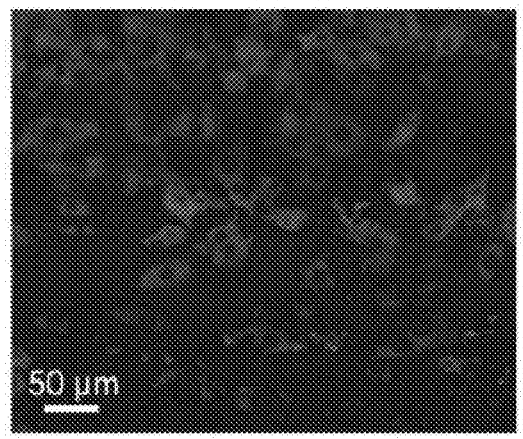
Figure 4F:
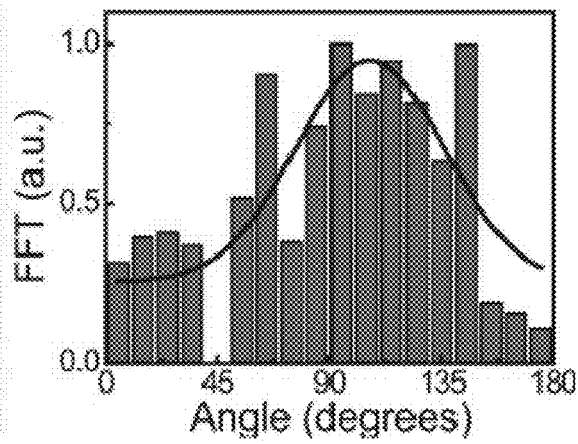
Figure 12:
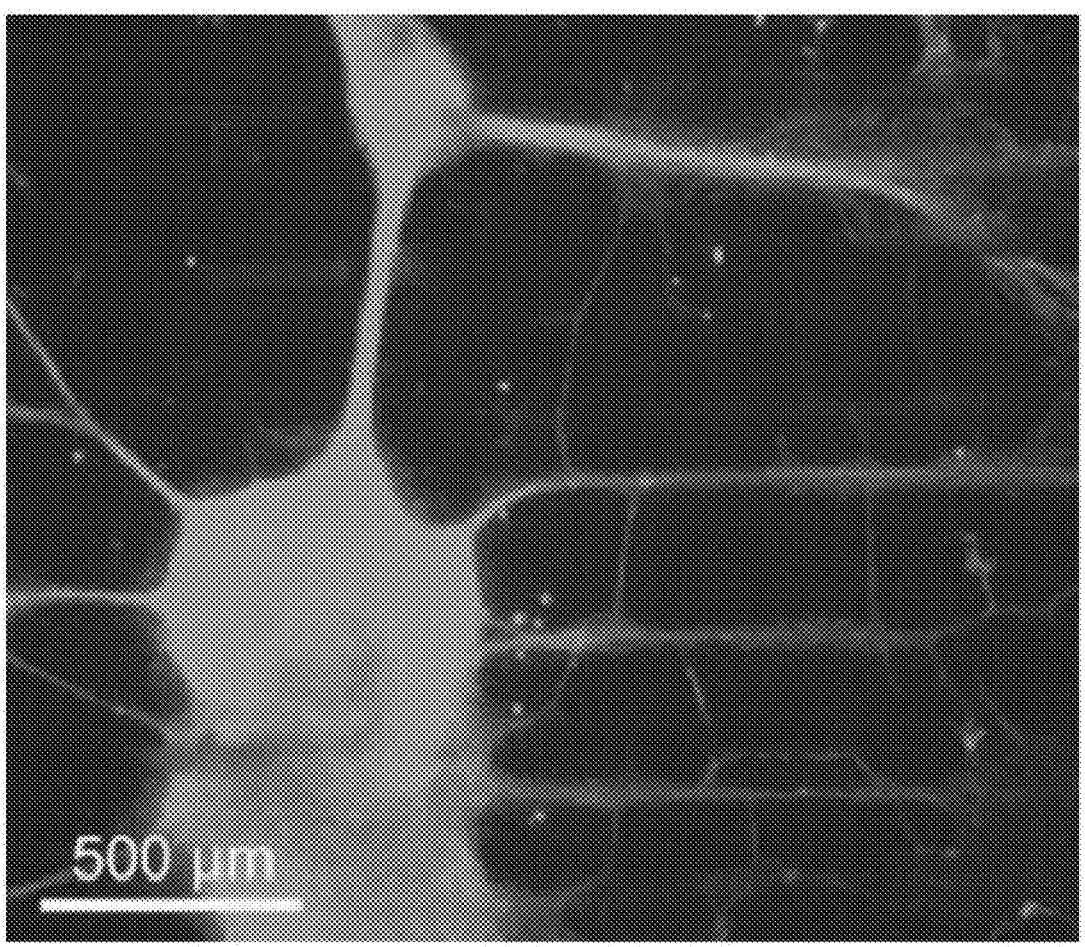
FIG. 12 illustrates non-limiting growth of dorsal root ganglia on diced 3D printed nerve guides. The image shows neurite network alignment with the horizontally oriented physical cue.
Figure 13:
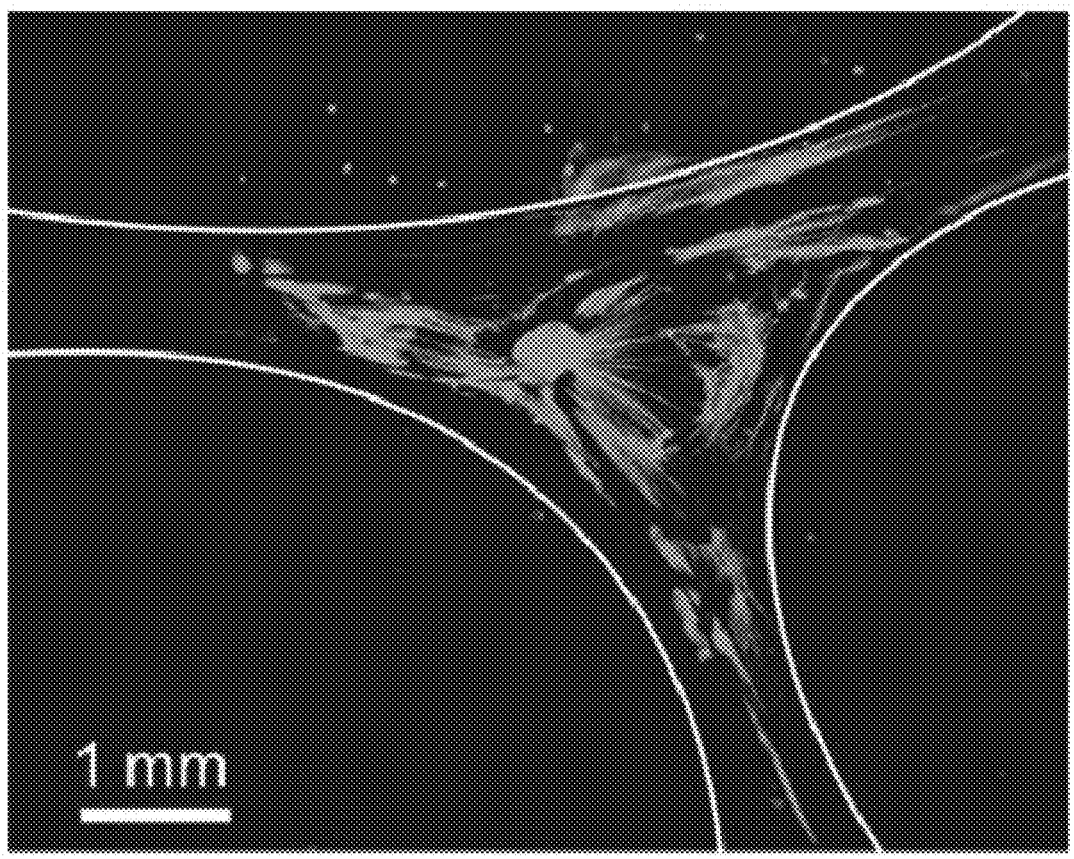
FIG. 13 illustrates non-limiting tau staining of sensory axon outgrowth from dorsal root ganglia in a 3D printed bifurcating nerve guide.
Figure 14:
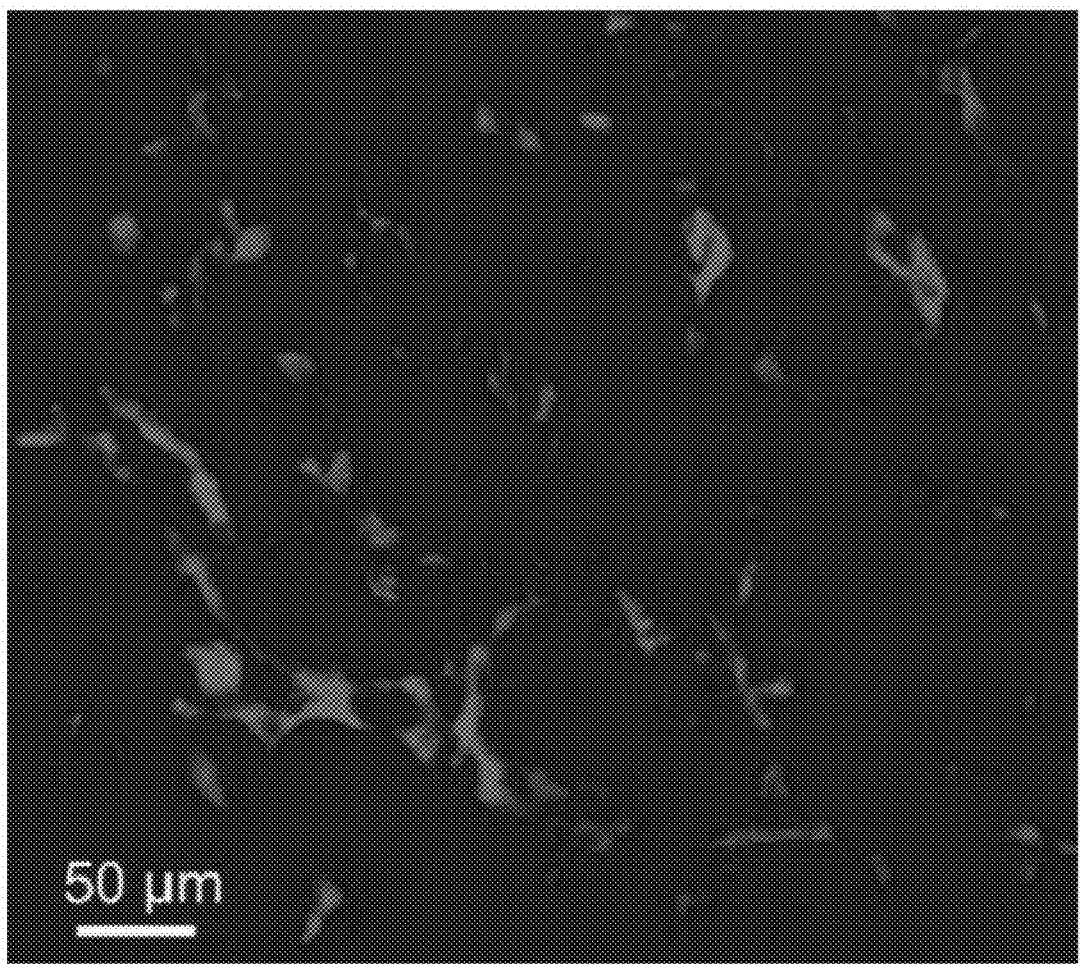
FIG. 14 illustrates non-limiting S100 staining of regenerated nerve reveals the presence of Schwann cells in both sensory and motor pathways (representative data from sensory pathway illustrated herein).
Figure 15:
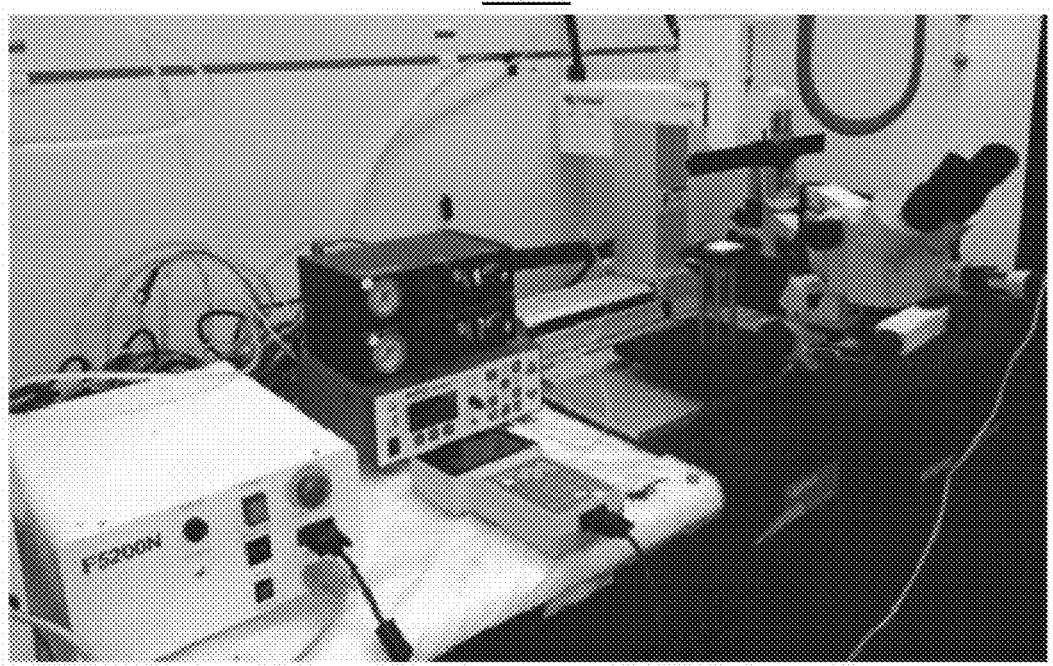
FIG. 15 illustrates a non-limiting photograph of the extrusion-based 3D printer highlighting the primary components, including the controller, the dispensing system, a three axes gantry robot, and a vision system.
Figure 16:
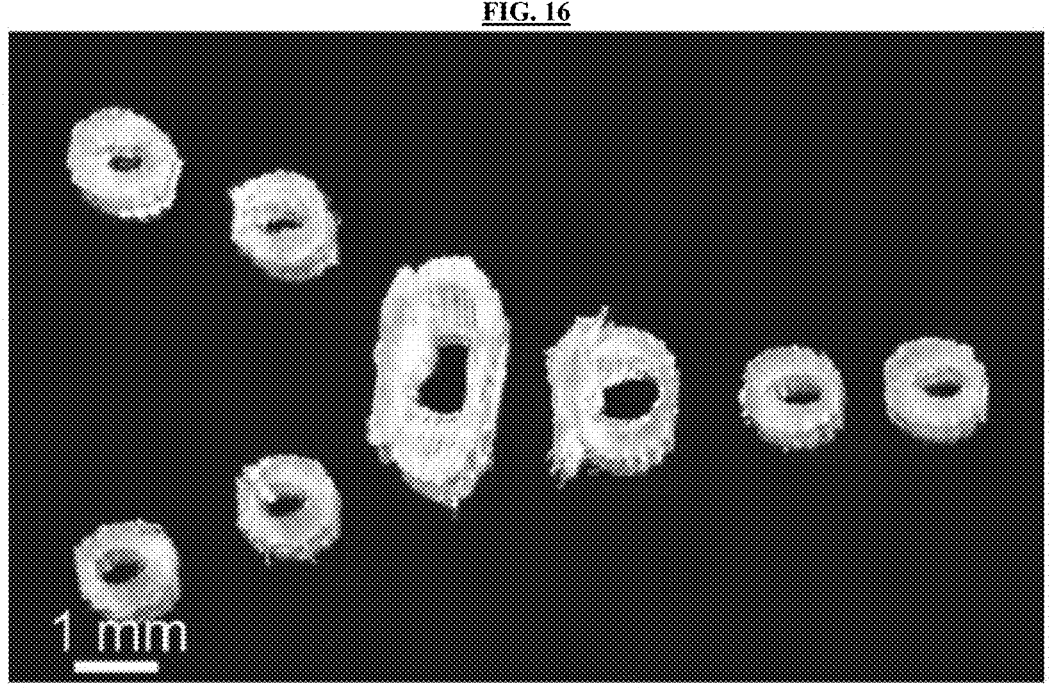
FIG. 16 illustrates non-limiting cross-sectional images of a 3D printed nerve guide at various positions along its length (L=10 mm; positions from left to right correspond to L, 0.75L, distal bifurcation region, proximal bifurcation region, 0.25L, and 0 mm).

It was then examined whether these 3D printed microgrooves affected the structures of regenerating axons and Schwann cells in vitro. FIG. 4C illustrates that the neurite network established by dissociated primary superior cervical ganglion (SCG) neurons on the 3D printed physical cue was highly aligned with an orientation coinciding with the printed physical cue (oriented at a 90° basis angle). This orientation was quantified via a fast Fourier transform (FFT) analysis, as illustrated in FIG. 4D. Control studies done in the absence of the 3D printed physical cue showed no such alignment, resulting in a randomly distributed neurite network (FIG. 11). Additional experiments were also done with dorsal root ganglia instead of dissociated SCG neurons, which similarly exhibited alignment of the neurite network with the physical cue (FIG. 12). Schwann cells cultivated on the 3D printed physical cue also adopted an orientation that aligned with the physical cue (FIGS. 4E-4F), especially in the vicinity of the microgroove.

Figure 5A:
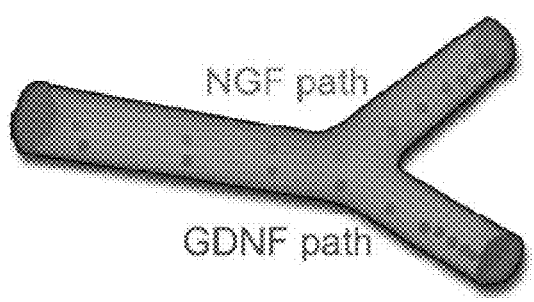
FIGS. 5A-5D illustrate non-limiting functionalization of nerve pathways with path-specific biochemical gradients.
Figure 5B:
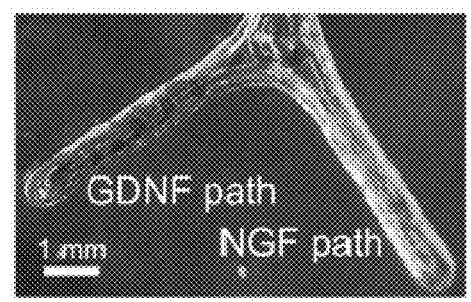

Example 5: Functionalization of Pathways with Multicomponent Biomolecular Gradients End-organ connections act as guides for selective re-innervation of sensory and motor paths. Studies were performed to further optimize the potential for selective re-innervation of each path by using 3D printing to introduce uniquely selective biochemical gradients within each path according to the strategy illustrated in FIG. 5A. Nerve growth factor (NGF) was selected as the non-limiting selective sensory path cue, and glial cell line-derived neurotrophic factor (GDNF) was selected as the non-limiting motor path cue, given their differential expression profiles in sensory and motor nerves. Gelatin hydrogel was selected as the encapsulation medium, given its high degree of neurocompatibility. As representatively illustrated in FIG. 5B, the hydrogel was printed in a spatial gradient distribution concentrated towards the distal end of each path, to provide a continuously enriching attractant. The hydrogel in the sensory path was loaded with NGF, while the hydrogel in the motor path was loaded with GDNF.

Figure 5C:
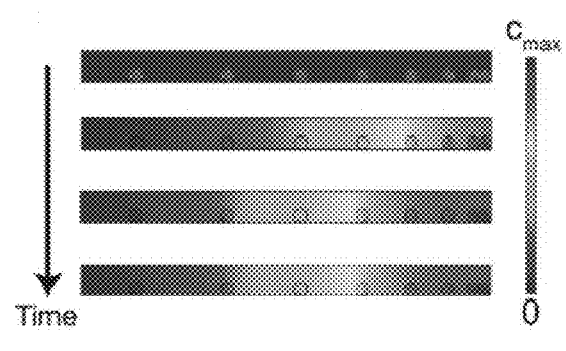
Figure 5D:
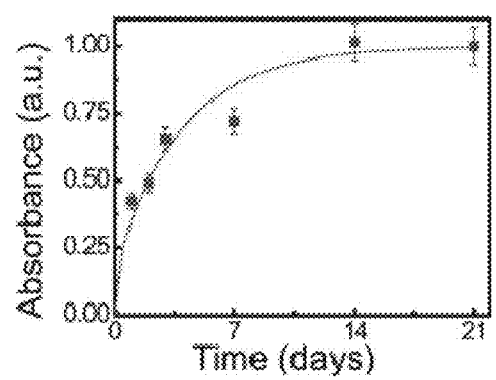

It was then confirmed that the 3D printed biochemical cues establishes an axial spatiotemporal gradient within each nerve pathway. The release of protein from the hydrogel occurs via a diffusive release mechanism. As illustrated in FIG. 5C, FEA of a representative 3D printed hydrogel configuration indeed results in an axial gradient within the inside of the nerve pathway, which is concentrated at the distal end and stretches across the full thickness of the guide. Thus, the presence of a higher relative concentration of biochemical cue in the distal end of the pathway provides a driving force for the regenerating sensory and motor nerves to re-innervate the proper distal organ pathways. The typical regeneration period of a peripheral nerve injury is at least three to four weeks, so the kinetics of protein release from the hydrogel system was examined to confirm that the time scale would be suitable. As shown in FIG. 5D, the controlled protein release was maintained over a three week period. A standard drug release model previously used for the analysis of hydrogel systems was also fit to the data:

$$\theta(t) = 1 - \frac{8}{\pi^2} \sum_{n=0}^{\infty} \frac{1}{(2n+1)^2} \exp\left(\frac{-D(2n+1)^2 \pi^2 t}{L^2}\right) \quad (1)$$

where $\theta(t)$ is the fraction released, t is the time, L is the film thickness, and D is the diffusivity. Using the diffusivity as a single fitting parameter, the effective protein diffusivity in the hydrogel system was estimated for use in FEA studies.

Example 6: 3D Printed Pathways for Regeneration: in vitro and in vivo Studies

Figure 6A:
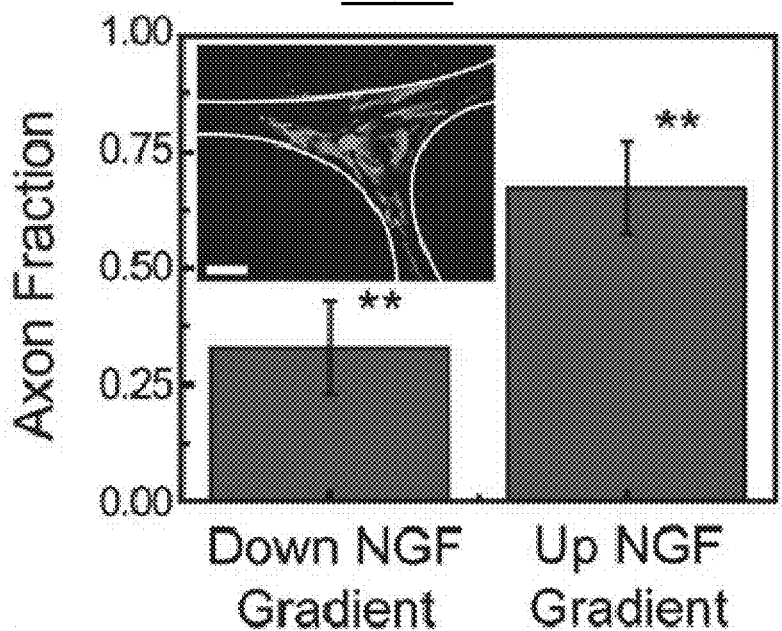
FIGS. 6A-6C illustrate non-limiting in vitro and in vivo characterization of regeneration with 3D printed nerve pathways.

Studies were performed to examine effects of NGF and GDNF on axon and Schwann cell responses when implemented in diffusive gradients. The effect of a diffusive NGF gradient on the formation of sensory neurite networks in vitro was examined. As illustrated in FIG. 6A, 67% of axons were attracted towards the source, in comparison with 49% observed in control studies lacking the gradient, indicating that the diffusive NGF gradients acted as a chemotractant for sensory axons ($p<0.01$).

Having established that the NGF gradient selectively attracts sensory axons, the potential for the GDNF gradient to improve selective innervation of the motor path via its effect on supporting Schwann cells was examined. There is a higher abundance of Schwann cells in sensory nerve pathways, which act as a potential mechanism by which motor axons improperly enter sensory pathways during regeneration.

Figure 6B:
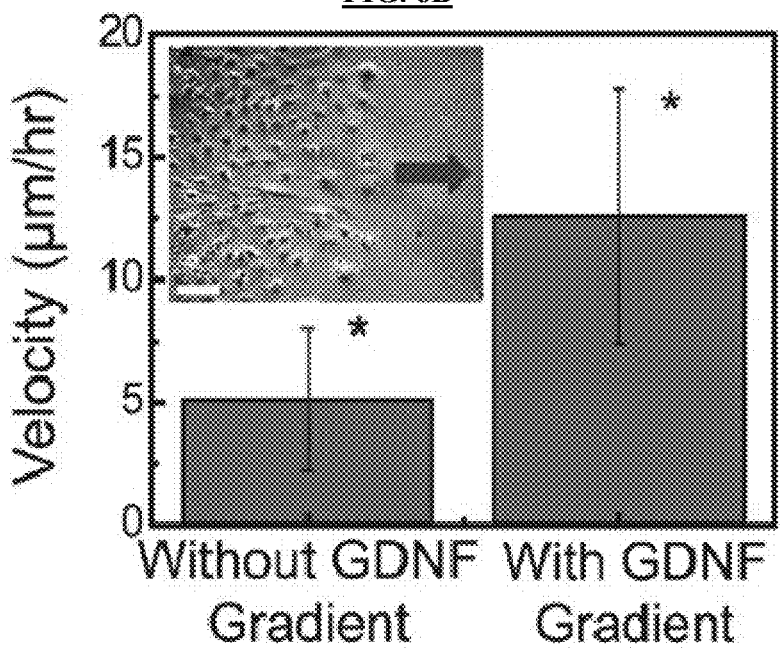

It was studied whether the GDNF gradient has an effect on the Schwann cell migration velocity, which could beneficially impact the relative repopulations of the sensory and motor pathways during regeneration. As illustrated in FIG. 6B, the diffusive GDNF gradient acted as a chemokinetic cue, which caused an increase in the Schwann cell migration velocity from 5.1 to 12.6 µm/h ($p<0.05$). Based on this relative increase in migration velocity, the GDNF gradient can serve to increase the population of Schwann cells in the motor pathway, thereby mitigating one of the potential mechanisms by which motor nerves improperly re-innervate sensory pathways.

Figure 6C:
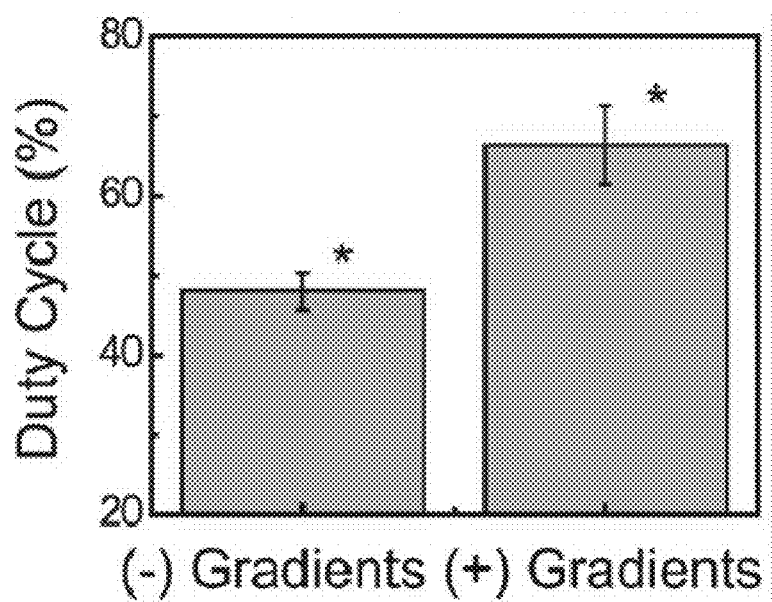

Having demonstrated various advantages offered by the 3D printing approach in terms of geometric, physical, and biochemical customization in vitro, a preliminary small animal study was performed to investigate the use of this technology for in vivo regeneration. The regeneration of a 10 mm complex nerve gap injury to the sciatic nerve bifurcation was examined over a 3 month period. Specifically, it was of interest to determine whether the gradients provided any significant improvement on the functional return of the regenerated bifurcating mixed nerve. Detailed gait analysis of the rats indeed revealed significant improvement in the functional return of the limbs treated with the 3D printed nerve scaffolds which were augmented with path-specific biochemical gradients. As illustrated in FIG. 6C, significant improvement was observed with respect to the gait duty cycle: an improvement by a factor of 1.4 ($p<0.05$) relative to performance in guides lacking the 3D printed gradient. In certain embodiments, 3D printing can be applied to successfully regenerate complex bifurcating mixed nerve injuries in vivo. In other embodiments, functionalizing the nerve pathway with 3D printed path-specific biochemical gradients results in enhanced functional return of regenerated complex nerve tissue, which contains bifurcating sensory and motor nerve pathways.

As demonstrated herein, the present invention provides a novel 3D printing approach for nerve regeneration pathways that are personalized to anatomical geometry, and contain advantageous augmentation with physical and biochemical cues to promote the simultaneous regeneration of multiple nerve pathways. This represents an exemplary illustration that imaging-coupled 3D printing approaches can facilitate customized neuroregeneration in previously inaccessible ways. 3D scanning allows matching the final pathway geometric design to the original tissue structure. Mechanical and computational tools allow designing, analyzing, and optimizing the integrity of the pathways. A one-pot 3D printing process provides the ability to introduce advantageous physical and biochemical cues in the form of microgrooves and multicomponent diffusive biomolecular gradients. This combination of complex geometries and sophisticated supporting cues allows for the regeneration of complex mixed nerve injuries.

The disclosures of each and every patent, patent application, and publication cited herein are hereby incorporated herein by reference in their entirety.

While the present invention has been disclosed with reference to specific embodiments, it is apparent that other embodiments and variations of this invention may be devised by others skilled in the art without departing from the true spirit and scope of the present invention. The appended claims are intended to be construed to include all such embodiments and equivalent variations.

What is claimed is:

1. A method of producing a 3D subject-specific biomimetic nerve conduit for use to replace a damaged section of a nerve pathway of a mammal, the method comprising:
    obtaining a primary 3D image by operating an imaging system to capture at least one image of bodily tissue, the at least one image being selected from the group consisting of: a damaged section of the nerve pathway of the mammal; and an intact nerve pathway of a similar mammal;
    generating a 3D computer model from the primary 3D image; and
    using the 3D computer model to 3D print a biomimetic nerve conduit that has a geometry corresponding to the damaged section of the mammal's nerve pathway, wherein the biomimetic nerve conduit comprises at least one motor branch and at least one sensory branch.

2. The method of claim 1, wherein a plurality of longitudinally extending indentations is present along the inner surface of at least one tube wall of the biomimetic nerve conduit.

3. The method of claim 2, wherein the plurality of longitudinally extending indentations have at least one geometry selected from the group consisting of a microgroove and a fiber.

4. The method of claim 2, wherein at least one of the plurality of longitudinally extending indentations has a geometry corresponding to a band of Büngner.

5. The method of claim 2, wherein at least one of the plurality of longitudinally extending indentations determines orientation of at least one peripheral nerve cell that locates to or grows in the lumen in the at least one tube wall, wherein the at least one peripheral nerve cell comprises at least one selected from the group consisting of axon and Schwann cell, whereby at least one of the plurality of longitudinally extending indentations provides a physical cue for the localization or growth of the at least one peripheral nerve cell.

6. The method of claim 1, wherein a plurality of droplets is distributed in a spatial relationship along the longitudinal dimension of at least one tube.

7. The method of claim 6, wherein the plurality of droplets comprises a hydrogel containing an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of droplets.

8. The method of claim 7, wherein the diffusion of the agent from the plurality of hydrogel droplets attracts or allows the growth of the at least one peripheral nerve cell, whereby the diffusion of the agent provides a biochemical cue for re-enervation of at least a portion of the biomimetic nerve conduit.

9. A method of producing a subject-specific biomimetic nerve conduit for use to replace a missing or damaged section of a nerve pathway of a subject mammal, the method comprising:
obtaining a primary image by capturing at least one image of bodily tissue of the subject, the image being selected from the group consisting of: an image of a region of the missing or damaged section of the nerve pathway of the subject mammal;
generating a 3D computer model from the primary image; and
using the 3D computer model to print a 3D biomimetic nerve conduit that has a geometry corresponding to the missing or damaged section of the mammal's nerve pathway.

10. The method of claim 9, wherein using the 3D computer model to print a 3D biomimetic nerve conduit that has a geometry corresponding to the missing or damaged section of the mammal's nerve pathway comprises printing at least one motor branch and at least one sensory branch.

11. The method of claim 9, wherein using the 3D computer model to print a 3D biomimetic nerve conduit comprises providing a plurality of longitudinally extending indentations is present along the inner surface of the biomimetic nerve conduit.

12. The method of claim 11, wherein providing the plurality of longitudinally extending indentations along an inner surface of the biomimetic nerve conduit comprises providing longitudinally extending indentations having at least one geometry selected from the group consisting of a microgroove and a fiber.

13. The method of claim 11, providing the plurality of longitudinally extending indentations along an inner surface of the biomimetic nerve conduit comprises providing longitudinally extending indentations having a geometry corresponding to a band of Büngner.

14. The method of claim 11, wherein providing the plurality of longitudinally extending indentations along an inner surface of the biomimetic nerve conduit comprises providing a physical cue determining orientation for the localization or growth of at least one peripheral nerve cell to locate to or grow in a lumen of the biomimetic nerve conduit, wherein the at least one peripheral nerve cell comprises at least one selected from the group consisting of axon and Schwann cell.

15. The method of claim 9, wherein using the 3D computer model to print a 3D biomimetic nerve conduit having a geometry corresponding to the missing or damaged section of the mammal's nerve pathway comprises providing a plurality of droplets distributed in a spatial relationship along a longitudinal dimension of the biomimetic nerve conduit.

16. The method of claim 15, wherein providing the plurality of droplets distributed in a spatial relationship along a longitudinal dimension of the biomimetic nerve conduit comprises providing a plurality of hydrogel droplets containing an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets.

17. The method of claim 16, wherein providing the plurality of hydrogel droplets comprises providing a biochemical cue for re-enervation of at least a portion of the biomimetic nerve conduit resulting from diffusion of the agent from the plurality of hydrogel droplets to attract or allow the growth of the at least one peripheral nerve cell.

18. A method of producing a biomimetic nerve conduit, the method comprising:
obtaining a primary image by 3D scanning bodily tissue to capture at least one image of bodily tissue, the image being selected from the group consisting of: a damaged or intact section of a nerve pathway of a mammal;
generating a 3D computer model from the primary image; and
printing, using additive manufacturing and the 3D computer model, a 3D biomimetic nerve conduit having a geometry corresponding to the damaged section of the mammal's nerve pathway.

19. The method of claim 18, wherein printing the 3D biomimetic nerve conduit comprises providing a plurality of longitudinally extending indentations along an inner surface of the biomimetic nerve conduit.

20. The method of claim 19, wherein providing the plurality of longitudinally extending indentations along an inner surface of the biomimetic nerve conduit comprises providing longitudinally extending indentations having at least one geometry selected from the group consisting of a microgroove and a fiber.

21. The method of claim 19, providing the plurality of longitudinally extending indentations along an inner surface of the biomimetic nerve conduit comprises providing longitudinally extending indentations having a geometry corresponding to a band of Büngner.

22. The method of claim 19, wherein providing the plurality of longitudinally extending indentations along an inner surface of the biomimetic nerve conduit comprises providing a physical cue determining orientation for the localization or growth of at least one peripheral nerve cell to locate to or grow in a lumen of the biomimetic nerve conduit, wherein the at least one peripheral nerve cell comprises at least one selected from the group consisting of axon and Schwann cell.

23. The method of claim 18, wherein printing, using the 3D computer model, the 3D biomimetic nerve comprises providing a plurality of droplets distributed in a spatial relationship along a longitudinal dimension of the biomimetic nerve conduit.

24. The method of claim 23, wherein providing the plurality of droplets distributed in a spatial relationship along a longitudinal dimension of the biomimetic nerve conduit comprises providing a plurality of hydrogel droplets containing an agent selected from a micro RNA, a single stranded DNA, a double stranded DNA, a cell, a filler, a therapeutic drug, a chemoattractant, a biocide, a peptide, a protein, a chemoattractant, a catalyst and any combinations thereof, wherein the agent is capable of diffusing from the plurality of hydrogel droplets.

25. The method of claim 24, wherein providing the plurality of hydrogel droplets comprises providing a biochemical cue for re-enervation of at least a portion of the biomimetic nerve conduit resulting from diffusion of the agent from the plurality of hydrogel droplets to attract or allow the growth of the at least one peripheral nerve cell.

* * * * *

UNITED STATES PATENT AND TRADEMARK OFFICE
CERTIFICATE OF CORRECTION

| | | |
|---|---|---|
| PATENT NO. | : 10,405,963 B2 | Page 1 of 1 |
| APPLICATION NO. | : 14/942714 | |
| DATED | : September 10, 2019 | |
| INVENTOR(S) | : McAlpine et al. | |

It is certified that error appears in the above-identified patent and that said Letters Patent is hereby corrected as shown below:

On the Title Page

Item (72) Inventor is corrected to read:
-- Michael C. McAlpine, Minneapolis, MN (US);
Blake N. Johnson, Plainsboro, NJ (US);
Karen Z. Lancaster, Hurst (TX). --

Signed and Sealed this
Fifth Day of November, 2024

Katherine Kelly Vidal
*Director of the United States Patent and Trademark Office*